US005767041A

United States Patent [19]

Schallner et al.

[11] Patent Number: 5,767,041

[45] Date of Patent: Jun. 16, 1998

[54] HERBICIDAL ARYLIMINO-SUBSTITUTED TRIAZOLES, THIADIAZOLES OR OXADIAZOLES

[75] Inventors: Otto Schallner, Monheim; Andreas Lender, Wuppertal; Hans-Joachim Santel; Markus Dollinger, both of Leverkusen, all of Germany

[73] Assignee: Bayer Aktiengesellschaft, Leverkusen, Germany

[21] Appl. No.: 776,267

[22] PCT Filed: Jun. 30, 1995

[86] PCT No.: PCT/EP95/02547

§ 371 Date: Jan. 7, 1997

§ 102(e) Date: Jan. 7, 1997

[87] PCT Pub. No.: WO96/02523

PCT Pub. Date: Feb. 1, 1996

[30] Foreign Application Priority Data

Jul. 14, 1994 [DE] Germany .......................... 44 24 787.7

[51] Int. Cl.[6] ...................... C07D 285/135; A01N 43/82

[52] U.S. Cl. .......................... 504/275; 504/263; 504/265; 544/134; 548/141; 548/144

[58] Field of Search .................................. 548/141, 144; 544/134; 504/263, 265, 225

[56] References Cited

U.S. PATENT DOCUMENTS 3,522,267 7/1970 Duerr et al. ............................ 548/141

FOREIGN PATENT DOCUMENTS 0 023 766 2/1981 European Pat. Off. .
0 300 906 1/1989 European Pat. Off. .
37 22 074 1/1989 Germany .

OTHER PUBLICATIONS

Tetrahedron, vol. 46, No. 12, pp. 4353–4370, Molina et al., "Heterocumulene–Mediated . . . Ring Systems".

Database Crossfire BRN 245450; Chem.Ber., vol. 37, 1904, pp. 2333–2346.

Database Crossfire BRN 30209, 268437 and 310513; J.Amer.Chem.Soc., vol. 26, 1904, pp. 1009–1018.

Database Crossfire BRN 980776, 5388149 and 5388442; Indian J.Chem., vol. 11, 1973, pp. 321–324.

Journal of Medicinal Chemistry, vol. 15, No. 6, 1972, Blank et al., "Synthesis of 1,2,4–triazoles as potential hypoglycemic agents".

Justus Liebigs Annalen Der Chemie, vol. 675, 1964, pp. 176–179, Gehlen et al., "2–Amino–5–. . . und Bromycan".

Journal of the Chemical Society, 1969, pp. 194–195, Davidson, "Some 1–aryl . . . 4–triazoles".

Journal of the Chemical Society, 1967, pp. 2471–2472, Davidsdon, "The Action of Hydrazine on Isodithiobiurets".

Database Crossfire BRN 5526948, 5532706, 5532707, 5532714, 5532863, 5532875, 5539797, 5544088, 5541557, 5548777, 5555904, 5558300, 5558892, 5558960, 5563987, 5566709, 5566725, 5567203; Z.Chem., vol. 20, No. 1, 1980, pp. 25–26.

Roberts Weed Res. 1968 8(2) 151 Abstract Only, Feb. 1968.

*Primary Examiner*—Robert Gerstl
*Attorney, Agent, or Firm*—Sprung Kramer Schaefer & Briscoe

[57] ABSTRACT

The invention relates to new substituted aryliminoheterocycles of the general formula (I)

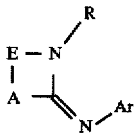

(I)

in which

A represents oxygen, sulphur or the group N—$R^1$ where $R^1$ represents hydrogen or in each case optionally substituted alkyl, alkenyl or akinyl, E represents one of the following groups

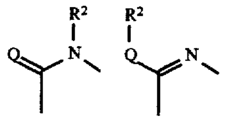

where Q represents oxygen, sulphur or the group N—$R^1$ (where $R^1$ has the abovementioned meaning) and $R^2$ represents hydrogen, cyano or in each case optionally substituted alkyl, alkenyl, alkinyl, cycloalkyl or cycloalkenyl, R represents hydrogen or in each case optionally substituted alkyl, alkenyl or alkinyl, and Ar represents in each case optionally substituted monocyclic or bicyclic aryl or heteroaryl, to processes for their preparation and to their use as herbicides.

5 Claims, No Drawings

HERBICIDAL ARYLIMINO-SUBSTITUTED TRIAZOLES, THIADIAZOLES OR OXADIAZOLES

This application is a 371 of PCT/EP95/02547 filed Jun. 30, 1995.

The invention relates to novel substituted aryliminoheterocycles, to processes for their preparation and to their use as herbicides.

Substituted aryliminoheterocycles have not been disclosed as yet as biologically active substances.

There have now been found novel substituted aryliminoheterocycles of the general formula (I)

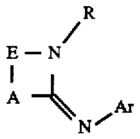

(I)

in which

A represents oxygen, sulphur or the group N—$R^1$ where $R^1$ represents hydrogen or in each case optionally substituted alkyl, alkenyl or alkinyl, E represents one of the following groups

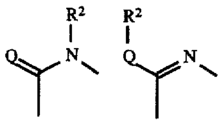

where

Q represents oxygen, sulphur or the group N—$R^1$ (where $R^1$ has the abovementioned meaning) and $R^2$ represents hydrogen, cyano or in each case optionally substituted alkyl, alkenyl, alkinyl, cycloalkyl or cycloalkenyl, R represents hydrogen or in each case optionally substituted alkyl, alkenyl or alkinyl, and Ar represents in each case optionally substituted monocyclic or bicyclic aryl or heteroaryl.

Thus, the general formula (I) represents the isomeric compounds of the general formulae (IA) and (IB) below.

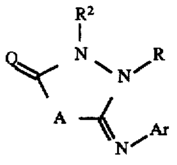

(IA)

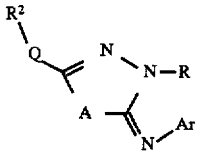

(IB)

The novel substituted aryliminoheterocycles of the general formula (I) are obtained when arylimino compounds of the general formula (II)

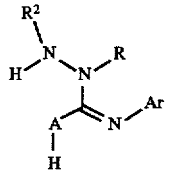

(II)

in which

A, R, $R^2$ and Ar have the abovementioned meanings—and/or compounds which are tautomeric to these—are cyclized with reactive carbonic acid derivatives of the general formula (III)

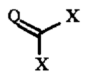

(III)

in which

Q has the abovementioned meaning and

X represents halogen, alkoxy, aryloxy or aralkoxy, if appropriate in the presence of a reaction auxiliary and if appropriate in the presence of a diluent and, if appropriate, the resulting compounds of the formulae (IA) and/or (IB), in the event that $R^2$ in these formulae represents hydrogen, are reacted with alkylating agents of the general formula (IV)

$R^2—X^1$ (IV)

in which $R^2$ has the abovementioned meaning with the exception of hydrogen and $X^1$ represents halogen or the group —O—$SO_2$—O—$R^2$, if appropriate in the presence of a reaction auxiliary and if appropriate in the presence of a diluent.

The novel substituted aryliminoheterocycles of the general formula (I) are distinguished by a powerful herbicidal activity.

In the definitions, the saturated or unsaturated hydrocarbon chains, such as alkyl, alkenyl or alkinyl, are in each case straight-chain or branched.

Halogen generally represents fluorine, chlorine, bromine or iodine, preferably fluorine, chlorine or bromine, in particular fluorine or chlorine.

The invention preferably relates to compounds of the formula (I) in which

A represents oxygen, sulphur or the group N—$R^1$ where $R^1$ represents hydrogen or represents alkyl having 1 to 6 carbon atoms which is optionally substituted by cyano, halogen, $C_1$–$C_4$-alkoxy, $C_1$–$C_4$-alkyl-carbonyl or $C_1$–$C_4$-alkoxy-carbonyl, or represents alkenyl or alkinyl each of which has 2 to 6 carbon atoms and each of which is optionally substituted by halogen, E represents one of the following groups

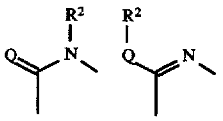

where

Q represents oxygen, sulphur or the group N—$R^1$ (where $R^1$ has the meaning given above as being preferred) and $R^2$ represents hydrogen, cyano, or represents alkyl having 1 to 6 carbon atoms which is optionally substituted by cyano, halogen, $C_1$–$C_4$-alkoxy, $C_1$–$C_4$-alkyl-carbonyl or $C_1$–$C_4$-alkoxy-carbonyl, or represents alkenyl or alkinyl each of which has 2 to 6 carbon atoms and each of which is optionally substituted by halogen, or represents cycloalkyl having 3 to 6 carbon atoms or cycloalkenyl having 5 or 6 carbon atoms each of which is optionally substituted by halogen or $C_1$–$C_4$-alkyl, R represents hydrogen or represents alkyl having 1 to 6 carbon atoms which is optionally substituted by cyano, halogen, $C_1$–$C_4$-alkoxy, $C_1$–$C_4$-alkyl-carbonyl or $C_1$–$C_4$-alkoxy-carbonyl, or represents alkenyl or alkinyl each of which has 2 to 6 carbon atoms and each of which is optionally substituted by halogen, and Ar represents one of the monocyclic or bicyclic aryl or heteroaryl groups below,

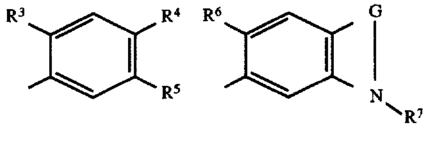

each of which is optionally substituted, and in which $R^3$ represents hydrogen or halogen, $R^4$ represents hydrogen, cyano, nitro, thiocarbamoyl, halogen, or in each case optionally halogen-substituted $C_1$–$C_4$-alkyl or $C_1$–$C_4$-alkoxy, $R^5$ represents the group below $$—A^1—A^2—A^3$$

in which $A^1$ represents a single bond, or represents oxygen, sulphur, —SO—, —$SO_2$—, —CO— or the group —N—$A^4$— where $A^4$ represents hydrogen, hydroxyl, $C_1$–$C_4$-alkyl, $C_1$–$C_4$-alkoxy, phenyl, $C_1$–$C_4$-alkylsulphonyl or phenylsulphonyl or $A^1$ furthermore represents $C_1$–$C_6$-alkanediyl, $C_2$–$C_6$-alkenediyl, $C_2$–$C_6$-azaalkenediyl, $C_2$–$C_6$-alkinediyl, $C_3$–$C_6$-cycloalkanediyl, $C_3$–$C_6$-cycloalkenediyl or phenylene, each of which is optionally substituted by fluorine, chlorine or bromine, $A^2$ represents a single bond, or represents oxygen, sulphur, —SO—, —$SO_2$—, —CO— or the group —N—$A^4$— where $A^4$ represents hydrogen, hydroxyl, $C_1$–$C_4$-alkyl, $C_1$–$C_4$-alkoxy, phenyl, $C_1$–$C_4$-alkylsulphonyl or phenylsulphonyl or $A^2$ furthermore represents $C_1$–$C_6$-alkanediyl, $C_2$–$C_6$-alkenediyl, $C_2$–$C_6$-azaalkenediyl, $C_2$–$C_6$-alkinediyl, $C_3$–$C_6$-cycloalkanediyl, $C_3$–$C_6$-cycloalkenediyl or phenylene, each of which is optionally substituted by fluorine, chlorine or bromine, $A^3$ represents hydrogen, hydroxyl, amino, cyano, isocyano, thiocyanato, nitro, carboxyl, carbamoyl, thiocarbamoyl, sulpho, chlorosulphonyl, halogen, or represents alkyl, alkoxy, alkylthio, alkylsulphinyl, alkylsulphonyl, alkylamino, dialkylamino, alkoxycarbonyl or dialkoxy(thio)phosphoryl, each of which has 1 to 6 carbon atoms in the alkyl groups and each of which is optionally substituted by halogen or $C_1$–$C_4$-alkoxy, or represents alkenyl, alkenyloxy, alkenylamino, alkylidenamino, alkenyloxycarbonyl, alkinyl, alkinyloxy, alkinylamino or alkinyloxycarbonyl, each of which has 2 to 6 carbon atoms in the alkenyl, alkylidene or alkinyl groups and each of which is optionally substituted by halogen or represents cycloalkyl, cycloalkyloxy, cycloalkylalkyl, cycloalkylalkoxy, cycloalkylidenamino, cycloalkyloxycarbonyl or cycloalkylalkoxycarbonyl, each of which has 3 to 6 carbon atoms in the cycloalkyl groups and, if appropriate, 1 to 4 carbon atoms in the alkyl groups and each of which is optionally substituted by halogen, cyano, carboxyl, $C_1$–$C_4$-alkyl and/or $C_1$–$C_4$-alkoxycarbonyl, or represents phenyl, phenyloxy, phenyl-$C_1$–$C_4$-alkyl, phenyl-$C_1$–$C_4$-alkoxy, phenyloxycarbonyl or phenyl-$C_1$–$C_4$-alkoxycarbonyl, each of which is optionally substituted by nitro, cyano, carboxyl, halogen $C_1$–$C_4$-alkyl, $C_1$–$C_4$-halogenoalkyl, $C_1$–$C_4$-alkoxy, $C_1$–$C_4$-halogenoalkyloxy and/or $C_1$–$C_4$-alkoxy-carbonyl, (in each case optionally fully or partially hydrogenated) pyrrolyl, pyrazolyl, imidazolyl, triazolyl, furyl, thienyl, oxazolyl, isoxazolyl, thiazdyl, isothiazolyl, oxadiazolyl, thiadiazolyl, pyridinyl, pyrimidinyl, triazinyl, pyrazolyl-$C_1$–$C_4$-alkyl, furyl-$C_1$–$C_4$-alkyl, thienyl-$C_1$–$C_4$-alkyl, oxazolyl-$C_1$–$C_4$-alkyl, isoxazol-$C_1$–$C_4$-alkyl,thiazol-$C_1$–$C_4$-alkyl,pyridinyl-$C_1$–$C_4$-alkyl, pyrimidinyl-$C_1$–$C_4$-alkyl, pyrazolylmethoxy, furylmethoxy, or represents perhydropyranylmethoxy or pyridylmethoxy, $R^6$ represents hydrogen or halogen, $R^7$ represents hydrogen, hydroxyl, or represents alkyl having 1 to 6 carbon atoms which is optionally substituted by cyano, halogen, $C_1$–$C_4$-alkoxy, $C_1$–$C_4$-alkyl-carbonyl or $C_1$–$C_4$-alkoxy-carbonyl, or represents alkenyl or alkinyl, each of which has 2 to 6 carbon atoms and each of which is optionally substituted by halogen, or represents cycloalkyl or cycloalkylalkyl, each of which has 3 to 6 carbon atoms in the cycloalkyl moiety and, if appropriate, 1 to 4 carbon atoms in the alkyl moiety and each of which is optionally substituted by halogen or $C_1$–$C_4$-alkyl, or represents alkoxy or alkenyloxy, each of which has up to 6 carbon atoms and each of which is optionally substituted by halogen, or represents benzyl or benzyloxy, each of which is optionally substituted by cyano, halogen, $C_1$–$C_4$-alkyl, $C_1$–$C_4$-halogenoalkyl, $C_1$–$C_4$-alkoxy or $C_1$–$C_4$-halogenoalkoxy, and G represents one of the following groups —O—CO—, —S—CO—, —O—C($R^8$,$R^9$)—CO—, —C($R^8$,$R^9$)—O—CO—, —C($R^8$,$R^9$)—C($R^8$,$R^9$)—, —C($R^8$,$R^9$)—C($R^8$, $R^9$)—CO—, —C($R^8$)=C($R^8$)—, —C($R^8$)=C($R^8$)—CO—, —C($R^8$,$R^9$)—CO—, —N($R^{10}$)—C($R^8$, $R^9$)—CO—, —C($R^8$)=N—, —O—CO—C($R^8$, $R^9$)— where $R^8$ and $R^9$ are identical or different and individually represent hydrogen or alkyl having 1 to 6 carbon atoms or together represent alkanediyl having 2 to 6 carbon atoms, and $R^{10}$ represents hydrogen or alkyl having 1 to 6 carbon atoms.

In particular, the invention relates to compounds of the formula (I) in which

A represents oxygen, sulphur or the group N—$R^1$ where $R^1$ represents hydrogen, or represents methyl, ethyl, n- or i-propyl, n-, i-, s- or t-butyl, each of which is optionally substituted by cyano, fluorine, chlorine, methoxy, ethoxy, acetyl, propionyl, methoxycarbonyl or ethoxycarbonyl, or represents propenyl, butenyl, propinyl or butinyl, each of which is optionally substituted by fluorine, chlorine or bromine, E represents one of the following groups

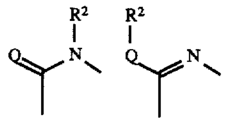

where

Q represents oxygen, sulphur or the group N—$R^1$ (where $R^1$ has the meaning given above as being particularly preferred) and $R^2$ represents hydrogen, cyano, or represents methyl, ethyl, n- or i-propyl, n-, i-, s- or t-butyl, each of which is optionally substituted by cyano, fluorine, chlorine, methoxy, ethoxy, acetyl, propionyl, methoxycarbonyl or ethoxycarbonyl, or represents propenyl, butenyl, propinyl or butinyl, each of which is optionally substituted by fluorine, chlorine or bromine, or represents cyclopentenyl or cyclohexenyl, R represents hydrogen, or represents methyl, ethyl, n- or i-propyl, n-, i-, s- or t-butyl, each of which is optionally substituted by cyano, fluorine, chlorine, methoxy, ethoxy, acetyl, propionyl, methoxycarbonyl or ethoxycarbonyl, or represents propenyl, butenyl, propinyl or butinyl, each of which is optionally substituted by fluorine, chlorine or bromine, and Ar represents one of the monocyclic or bicyclic aryl or heteroaryl groups below,

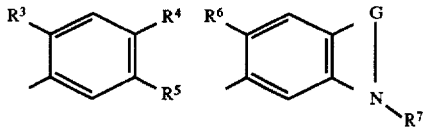

each of which is optionally substituted, in which $R^3$ represents hydrogen, fluorine or chlorine, $R^4$ represents hydrogen, cyano, chlorine, bromine, methyl or trifluoromethyl, $R^5$ represents the group below $$—A^1—A^2—A^3$$

in which $A^1$ represents a single bond, or represents oxygen, sulphur, —SO—, —$SO_2$—, —CO— or the group —N—$A^4$— where $A^4$ represents hydrogen, hydroxyl, methyl, ethyl, n- or i-propyl, methoxy, ethoxy, n- or i-propoxy, methylsulphonyl or ethylsulphonyl, or $A^1$ furthermore represents methylene, ethane- 1,1-diyl, ethane-1,2-diyl, propane-1,1-diyl, propane-1-2-diyl, propane-1-3-diyl, ethene-1,2-diyl, propene-1,2-diyl, propene-1-3-diyl, ethine-1,2-diyl or propine-1-3-diyl, $A^2$ represents a single bond, or represents oxygen, sulphur, —SO—, —$SO_2$—, —CO— or the group —N—$A^4$— where $A^4$ represents hydrogen, hydroxyl, methyl, ethyl, n- or i-propyl, methoxy, ethoxy, n- or i-propoxy, methylsulphonyl, ethylsulphonyl, n- or i-propylsulphonyl or phenylsulphonyl, or $A^2$ furthermore represents methylene, ethane-1,1-diyl, ethane-1,2-diyl, propane-1,1-diyl, propane-1-2-diyl, propane-1-3-diyl, ethene- 1,2-diyl, propene-1,2-diyl, propene-1-3-diyl, ethine-1,2-diyl or propine-1-3-diyl, $A^3$ represents hydrogen, hydroxyl, amino, cyano, nitro, carboxyl, carbamoyl, sulpho, fluorine, chlorine, bromine, or represents methyl, ethyl, n- or i-propyl, n-, i-, s- or t-butyl, n-, i-, s- or t-pentyl, methoxy, ethoxy, n- or i-propoxy, n-, i-, s- or t-butoxy, n-, i-, s- or t-pentyloxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, methoxycarbonyl, ethoxycarbonyl, n- or i-propoxycarbonyl, dimethoxyphosphoryl, diethoxyphosphoryl, dipropoxyphosphoryl or diisopropoxyphosphoryl, each of which is optionally substituted by fluorine, chlorine methoxy or ethoxy, or represents propenyl, butenyl, propenyloxy, butenyloxy, propenylamino, butenylamino, propylidenamino, butylidenamino, propenyloxycarbonyl, butenyloxycarbonyl, propinyl, butinyl, propinyloxy, butinyloxy, propinylamino, butinylamiino, propinyloxycarbonyl or butinyloxycarbonyl, each of which is optionally substituted by fluorine or chlorine, or represents cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl, cyclohexylmethyl, cyclopropyl-methoxy, cyclobutylmethoxy, cyclopentylmethoxy, cyclohexylmethoxy, cyclopentylidenamino, cyclohexylidenamino, cyclopentyloxycarbonyl, cyclohexyloxycarbonyl, cyclopentylmethoxycarbonyl or cyclohexyl-methoxycarbonyl, each of which is optionally substituted by fluorine, chlorine, cyano, carboxyl, methyl, ethyl, n- or i-propyl, methoxycarbonyl or ethoxycarbonyl, or represents phenyl, phenyloxy, benzyl, phenylethyl, benzyloxy, phenyloxycarbonyl, benzyloxycarbonyl, (in each case optionally fully or partially hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolylmethyl, furylmethyl, thienylmethyl, oxazolylmethyl, isoxazolmethyl, thiazolmethyl, pyridinylmethyl, pyrimidinylmethyl, pyrazolylmethoxy, furylmethoxy or pyridylmethoxy, each of which is optionally substituted by nitro, cyano, carboxyl, fluorine, chlorine, bromine, methyl, ethyl, n- or i-propyl, trifluoromethyl, methoxy, ethoxy, n- or i-propoxy, difluoromethoxy, trifluoromethoxy, methoxycarbonyl and/or ethoxycarbonyl, $R^6$ represents hydrogen, fluorine or chlorine, $R^7$ represents hydrogen, hydroxyl, or represents methyl, ethyl, n- or i-propyl, n-, i-, s- or t-butyl, each of which is optionally substituted by cyano, fluorine, chlorine, methoxy, ethoxy, acetyl, propionyl, methoxycarbonyl or ethoxycarbonyl, or represents propenyl, butenyl, propinyl or butinyl, each of which is optionally substituted by fluorine, chlorine or bromine, or represents cyclopropyl, cyclobutyl, cyclopentyl, cyclohexyl, cyclopropylmethyl cyclobutylmethyl, cyclopentylmethyl or cyclohexyl-methyl, each of which is optionally substituted by fluorine, chlorine, bromine, methyl or ethyl, or represents methoxy, ethoxy, n- or i-propoxy, n-, i- or s-butoxy, propenyloxy or butenyloxy, each of which is optionally substituted by fluorine and/or chlorine, or represents benzyl or benzyloxy, each of which is optionally substituted by cyano, fluorine, chlorine, bromine, methyl, ethyl, trifluoromethyl, methoxy, ethoxy, difluoromethoxy or trifluoromethoxy, and G represents one of the following groups —O—CO—, —S—CO—, —O—C($R^8$,$R^9$)—CO—, —C($R^8$,$R^9$)—O—CO—, —C($R^8$,$R^9$)—C($R^8$,$R^9$)—, —C($R^8$)=C($R^8$)—, —C($R^8$,$R^9$)—CO—, —N($R^{10}$)—C($R^8$,$R^9$)—CO—, —C($R^8$)=N—, O—CO—C($R^8$, $R^9$)— where $R^8$ and $R^9$ are identical or different and individually represent hydrogen, methyl, ethyl, n- or i-propyl or together represent ethane-1,2-diyl, and $R^{10}$ represents hydrogen, methyl, ethyl, n- or i-propyl.

The definitions of radicals given above, in general or where preferred ranges have been mentioned, apply both to the end products of the formula (I) and, analogously, to the starting materials or intermediates required in each case for the preparation. These definitions of radicals can be combined with each other as desired, that is to say combinations between the indicated ranges of preferred compounds are also possible.

Examples of the possible combinations of the above-defined groups A, Q, R, $R^2$ and Ar are listed below:

| A | Q | R | $R^2$ | Ar |
|---|---|---|---|---|
| S | O | $C_2H_5$ | $CH_3$ | 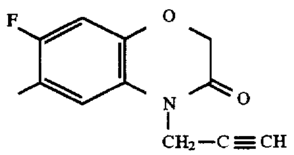 |
| S | O | $CH_3$ | $CH_2F$ | 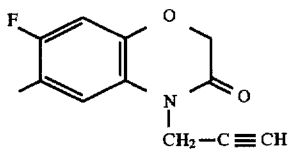 |
| S | O | $C_2H_5$ | $CHF_2$ | 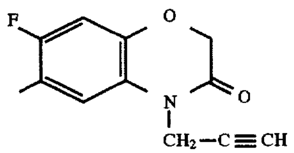 |
| S | O | $CH_3$ | $CF_3$ | 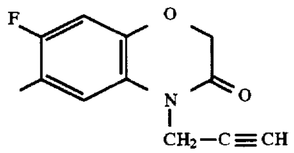 |
| S | O | $CHF_2$ | $C_2H_5$ | 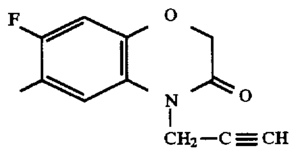 |
| S | O | $CHF_2$ | $CH_3$ | 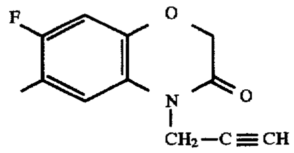 |
| S | O | 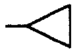 | $CHF_2$ | 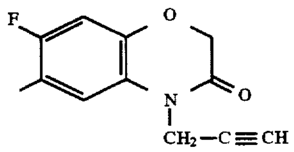 |
| S | O | 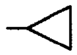 | $CH_3$ | 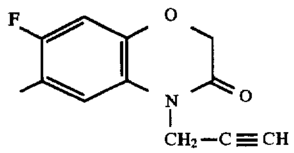 |

-continued
| A | Q | R | $R^2$ | Ar |
|---|---|---|---|---|
| S | O | $CH_3$ | 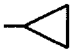 | 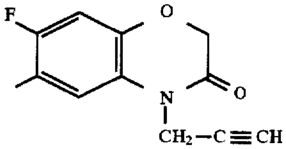 |
| S | O | n-$C_3H_7$ | $CHF_2$ | 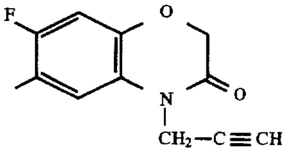 |
| S | O | n-$C_3H_7$ | $C_2H_5$ | 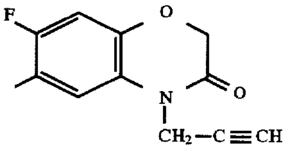 |
| S | O | n-$C_3H_7$ | $CH_3$ | 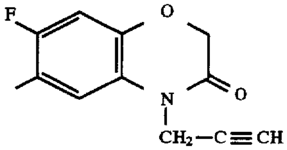 |
| S | O | $C_2H_5$ | $CH_2-C\equiv CH$ | 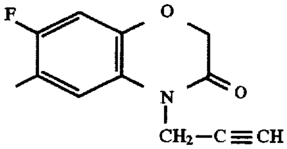 |
| S | O | $C_2H_5$ | $CH_2-CH=CH_2$ | 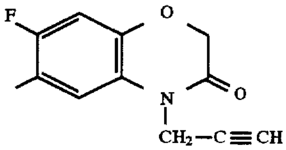 |
| S | O | $C_2H_5$ | $CH_2F$ | 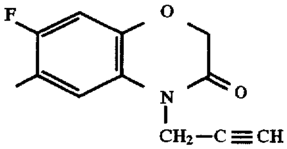 |
| S | O | $C_2H_5$ | $CH_3$ | 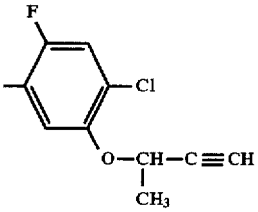 |
| S | O | $CH_3$ | $CH_2F$ | 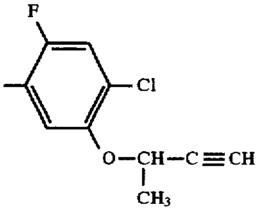 |

-continued
| A | Q | R | $R^2$ | Ar |
|---|---|---|---|---|
| S | O | $C_2H_5$ | $CHF_2$ | 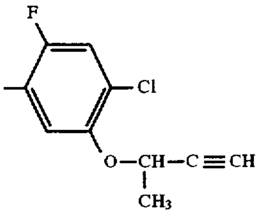 |
| S | O | $CH_3$ | $CF_3$ | 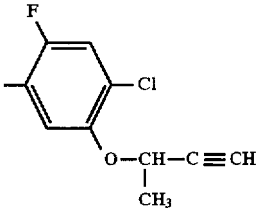 |
| S | O | $CHF_2$ | $C_2H_5$ | 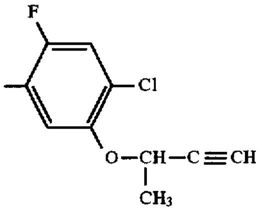 |
| S | O | $CHF_2$ | $CH_3$ | 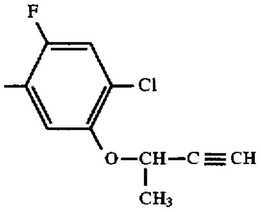 |
| S | O | 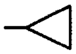 | $CHF_2$ | 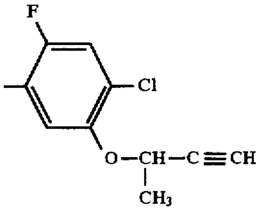 |
| S | O | 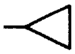 | $CH_3$ | 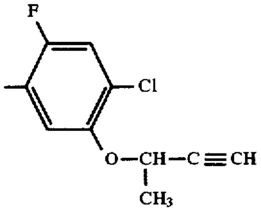 |
| S | O | $CH_3$ | 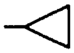 | 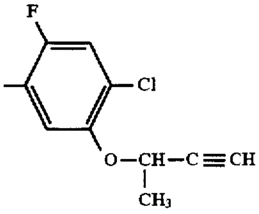 |

-continued
| A | Q | R | $R^2$ | Ar |
|---|---|---|---|---|
| S | O | n-$C_3H_7$ | $CHF_2$ | 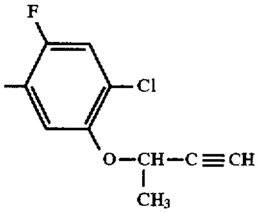 |
| S | O | n-$C_3H_7$ | $C_2H_5$ | 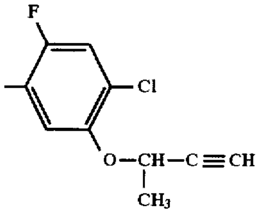 |
| S | O | n-$C_3H_7$ | $CH_3$ | 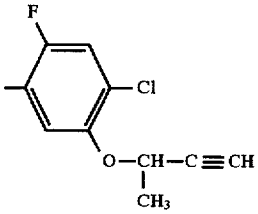 |
| S | O | $C_2H_5$ | $CH_2-C\equiv CH$ | 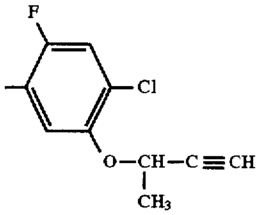 |
| S | O | $C_2H_5$ | $CH_2-CH=CH_2$ | 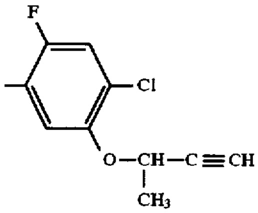 |
| S | O | $C_2H_5$ | $CH_2F$ | 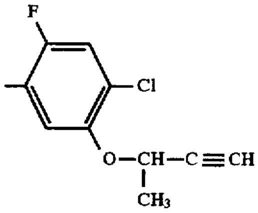 |
| S | O | $C_2H_5$ | $CH_3$ | 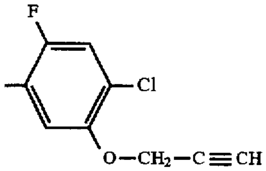 |

-continued
| A | Q | R | $R^2$ | Ar |
|---|---|---|---|---|
| S | O | $CH_3$ | $CH_2F$ | 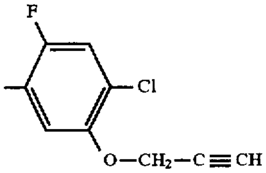 |
| S | O | $C_2H_5$ | $CHF_2$ | 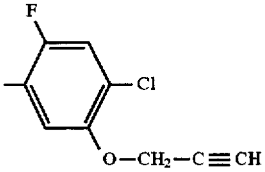 |
| S | O | $CH_3$ | $CF_3$ | 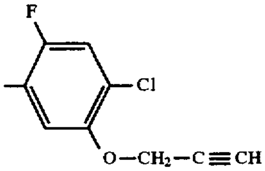 |
| S | O | $CHF_2$ | $C_2H_5$ | 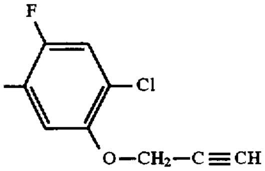 |
| S | O | $CHF_2$ | $CH_3$ | 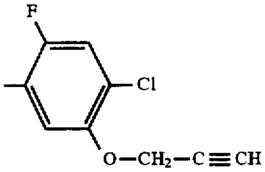 |
| S | O | 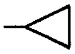 | $CHF_2$ | 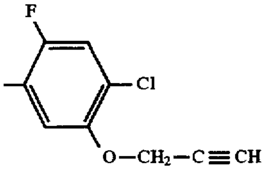 |
| S | O | 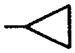 | $CH_3$ | 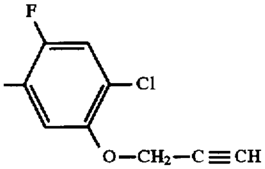 |
| S | O | $CH_3$ | 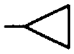 | 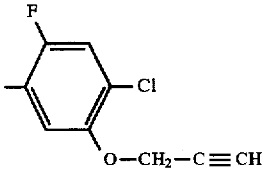 |

-continued
| A | Q | R | $R^2$ | Ar |
|---|---|---|---|---|
| S | O | $n\text{-}C_3H_7$ | $CHF_2$ | 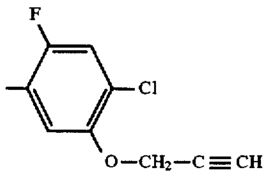 |
| S | O | $n\text{-}C_3H_7$ | $C_2H_5$ | 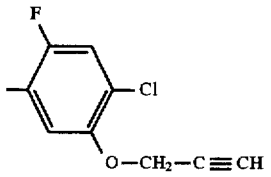 |
| S | O | $n\text{-}C_3H_7$ | $CH_3$ | 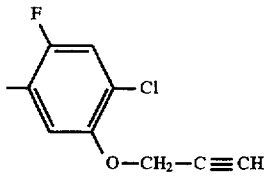 |
| S | O | $C_2H_5$ | $CH_2-C\equiv CH$ | 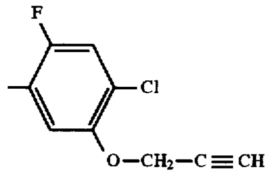 |
| S | O | $C_2H_5$ | $CH_2-CH=CH_2$ | 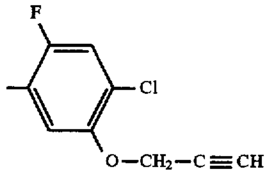 |
| S | O | $C_2H_5$ | $CH_2F$ | 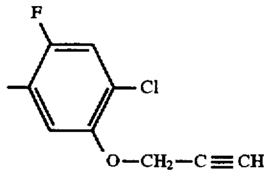 |
| S | O | $CH_3$ | $CH_3$ | 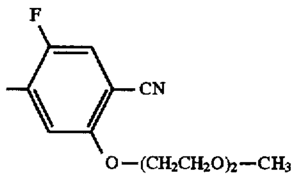 |
| S | O | $CH_3$ | $C_2H_5$ | 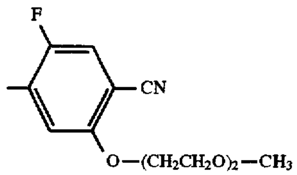 |

-continued
| A | Q | R | $R^2$ | Ar |
|---|---|---|---|---|
| S | O | $CH_3$ | $CH_2-CH=CH_2$ | 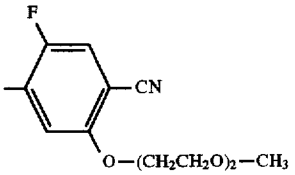 |
| S | O | $CH_3$ | $CH_2-C\equiv CH$ | 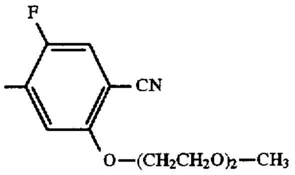 |
| S | O | $CH_3$ | $CHF_2$ | 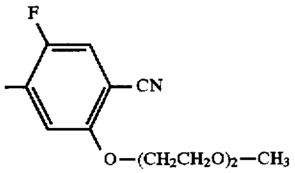 |
| S | O | $C_2H_5$ | $C_2H_5$ | 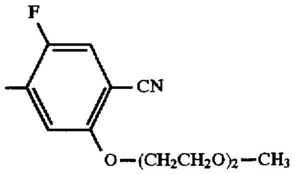 |
| S | O | $CH_3$ | $CH_2F$ | 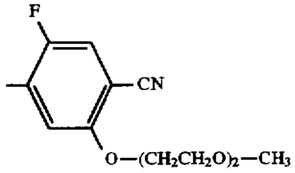 |
| S | O | $CH_3$ | $CF_3$ | 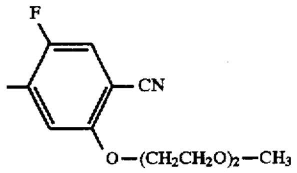 |
| S | O | $CH_3$ | $CH_3$ | 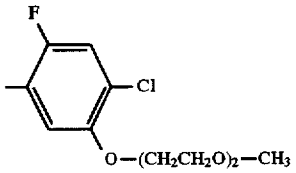 |
| S | O | $CH_3$ | $C_2H_5$ | 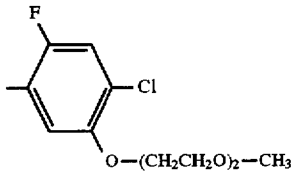 |

-continued
| A | Q | R | $R^2$ | Ar |
|---|---|---|---|---|
| S | O | $CH_3$ | $CH_2-CH=CH_2$ | 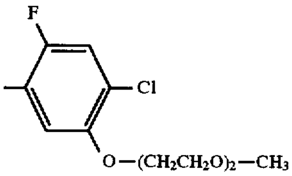 |
| S | O | $CH_3$ | $CH_2-C\equiv CH$ | 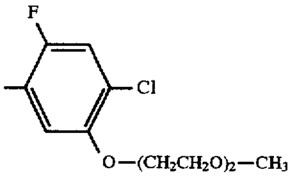 |
| S | O | $CH_3$ | $CHF_2$ | 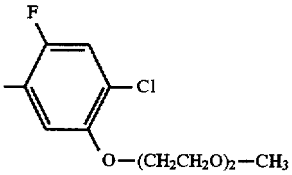 |
| S | O | $C_2H_5$ | $C_2H_5$ | 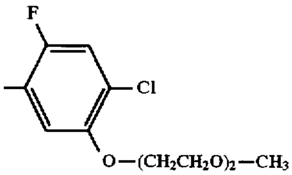 |
| S | O | $CH_3$ | $CH_2F$ | 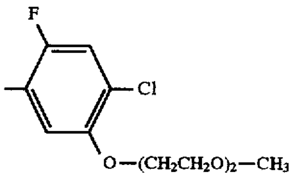 |
| S | O | $CH_3$ | $CF_3$ | 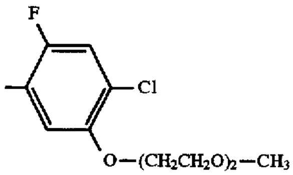 |
| S | O | $CH_3$ | $CH_3$ | 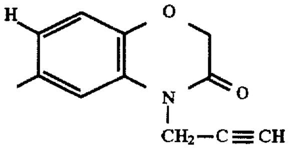 |
| S | O | $CH_3$ | $C_2H_5$ | 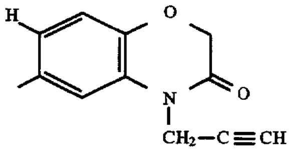 |
| S | O | $CH_3$ | $CH_2-CH=CH_2$ | 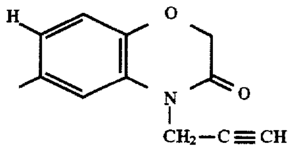 |

-continued
| A | Q | R | $R^2$ | Ar |
|---|---|---|---|---|
| S | O | $CH_3$ | $CH_2-C\equiv CH$ | 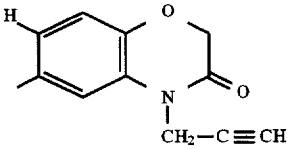 |
| S | O | $CH_3$ | $CHF_2$ | 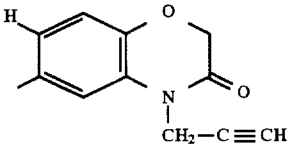 |
| S | O | $C_2H_5$ | $C_2H_5$ | 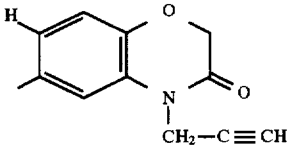 |
| S | O | $CH_3$ | $CH_2F$ | 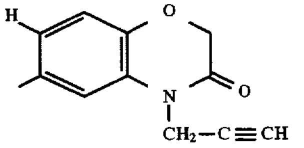 |
| S | O | $CH_3$ | $CF_3$ | 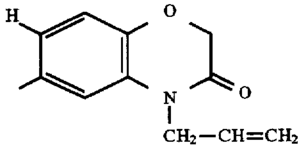 |
| S | O | $CH_3$ | $CH_3$ | 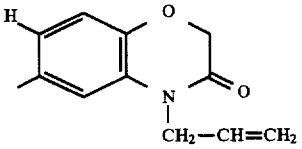 |
| S | O | $CH_3$ | $C_2H_5$ | 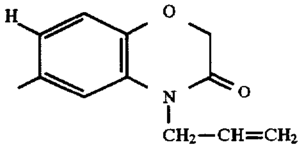 |
| S | O | $CH_3$ | $CH_2-CH=CH_2$ | 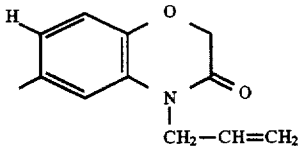 |
| S | O | $CH_3$ | $CH_2-C\equiv CH$ | 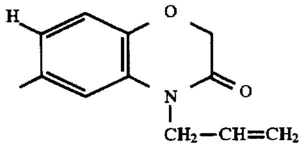 |
| S | O | $CH_3$ | $CHF_2$ | 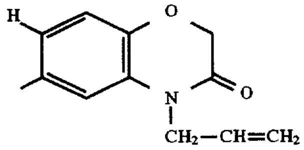 |

-continued
| A | Q | R | $R^2$ | Ar |
|---|---|---|---|---|
| S | O | $C_2H_5$ | $C_2H_5$ | 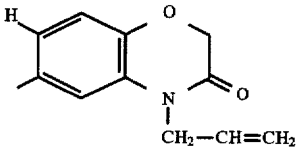 |
| S | O | $CH_3$ | $CH_2F$ | 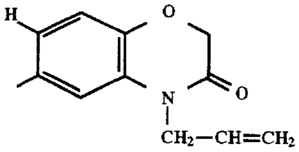 |
| S | O | $CH_3$ | $CF_3$ | 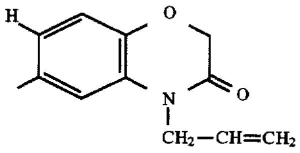 |
| S | O | $CH_3$ | $CH_3$ | 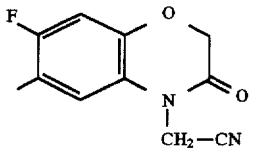 |
| S | O | $CH_3$ | $C_2H_5$ | 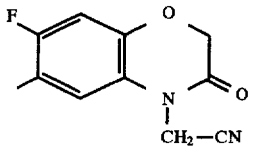 |
| S | O | $CH_3$ | $CH_2-CH=CH_2$ | 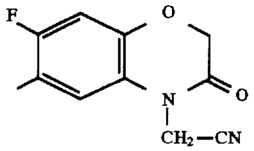 |
| S | O | $CH_3$ | $CH_2-C\equiv CH$ | 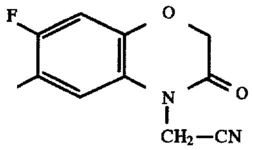 |
| S | O | $CH_3$ | $CHF_2$ | 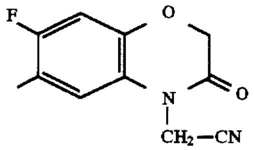 |
| S | O | $C_2H_5$ | $C_2H_5$ | 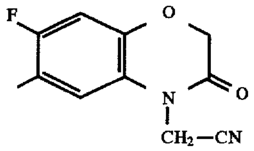 |
| S | O | $CH_3$ | $CH_2F$ | 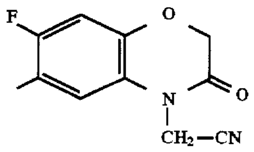 |

-continued
| A | Q | R | $R^2$ | Ar |
|---|---|---|---|---|
| S | O | $CH_3$ | $CF_3$ | 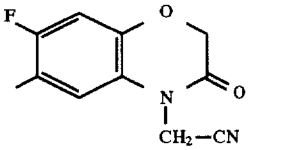 |
| S | O | $CH_3$ | $CH_3$ | 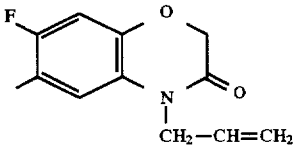 |
| S | O | $CH_3$ | $C_2H_5$ | 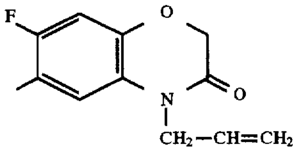 |
| S | O | $CH_3$ | $CH_2-CH=CH_2$ | 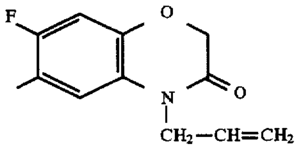 |
| S | O | $CH_3$ | $CH_2-C\equiv CH$ | 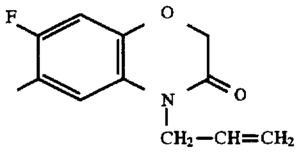 |
| S | O | $CH_3$ | $CHF_2$ | 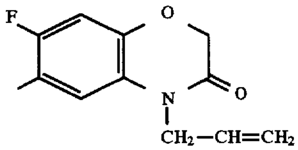 |
| S | O | $C_2H_5$ | $C_2H_5$ | 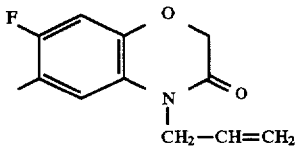 |
| S | O | $CH_3$ | $CH_2F$ | 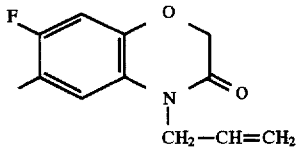 |
| S | O | $CH_3$ | $CF_3$ | 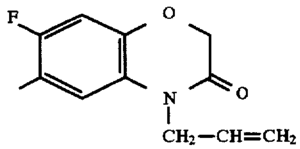 |
| S | O | $C_2H_5$ | $CH_3$ | 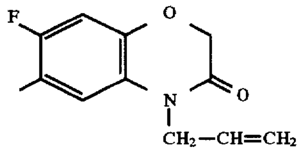 |

-continued
| A | Q | R | $R^2$ | Ar |
|---|---|---|---|---|
| S | O | $CH_3$ | $CH_2F$ | 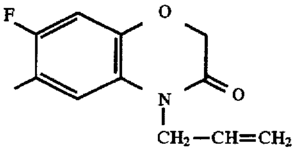 |
| S | O | $C_2H_5$ | $CHF_2$ | 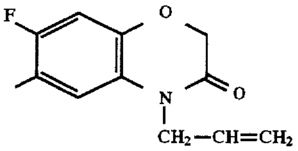 |
| S | O | $CH_3$ | $CF_3$ | 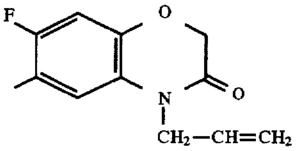 |
| S | O | $CHF_2$ | $C_2H_5$ | 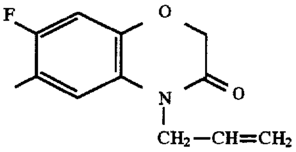 |
| S | O | $CHF_2$ | $CH_3$ | 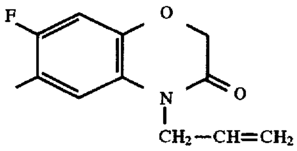 |
| S | O | 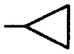 | $CHF_2$ | 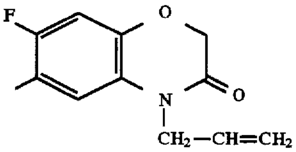 |
| S | O | 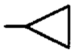 | $CH_3$ | 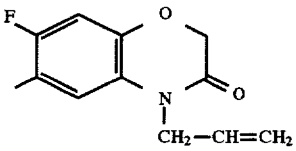 |
| S | O | $CH_3$ | 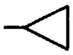 | 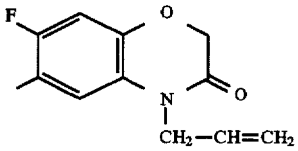 |
| S | O | n-$C_3H_7$ | $CHF_2$ | 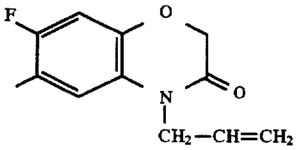 |
| S | O | n-$C_3H_7$ | $C_2H_5$ | 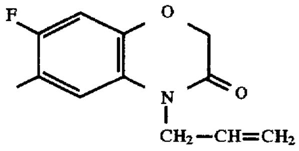 |

-continued
| A | Q | R | $R^2$ | Ar |
|---|---|---|---|---|
| S | O | $n\text{-}C_3H_7$ | $CH_3$ | 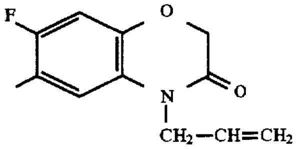 |
| S | O | $C_2H_5$ | $CH_2-CH_2-C\equiv CH$ | 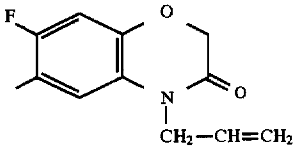 |
| S | O | $C_2H_5$ | $CH_2-CH=CH_2$ | 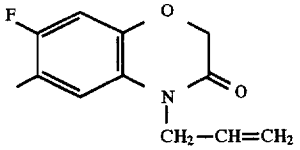 |
| S | O | $C_2H_5$ | $CH_2F$ | 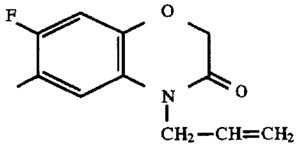 |
| S | O | $C_2H_5$ | $CH_3$ | 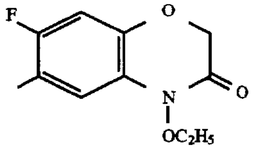 |
| S | O | $CH_3$ | $CH_2F$ | 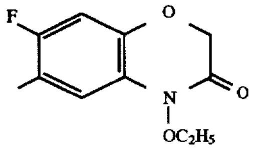 |
| S | O | $C_2H_5$ | $CHF_2$ | 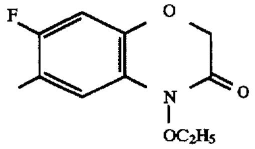 |
| S | O | $CH_3$ | $CF_3$ | 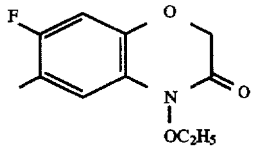 |
| S | O | $CHF_2$ | $C_2H_5$ | 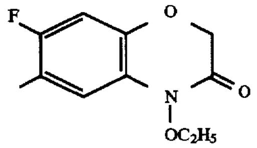 |
| S | O | $CHF_2$ | $CH_3$ | 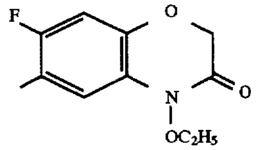 |

-continued
| A | Q | R | $R^2$ | Ar |
|---|---|---|---|---|
| S | O | 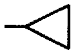 | $CHF_2$ | 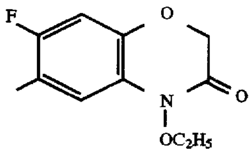 |
| S | O | 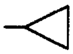 | $CH_3$ | 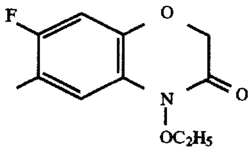 |
| S | O | $CH_3$ | 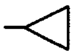 | 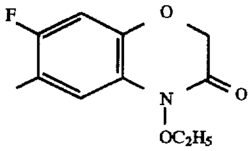 |
| S | O | n-$C_3H_7$ | $CHF_2$ | 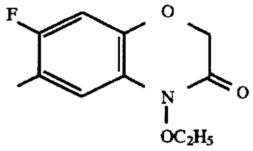 |
| S | O | n-$C_3H_7$ | $C_2H_5$ | 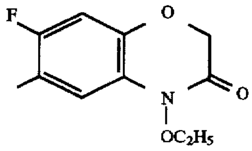 |
| S | O | n-$C_3H_7$ | $CH_3$ | 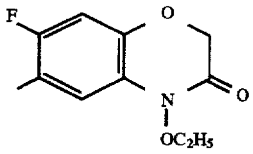 |
| S | O | $C_2H_5$ | $CH_2-C\equiv CH$ | 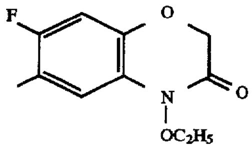 |
| S | O | $C_2H_5$ | $CH_2-CH=CH_2$ | 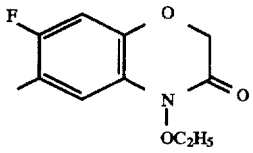 |
| S | O | $C_2H_5$ | $CH_2F$ | 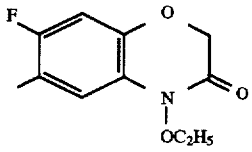 |
| S | O | $C_2H_5$ | $CH_3$ | 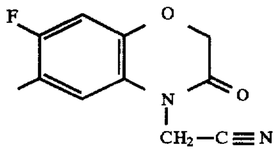 |

-continued
| A | Q | R | $R^2$ | Ar |
|---|---|---|---|---|
| S | O | $CH_3$ | $CH_2F$ | 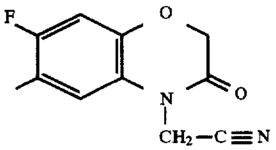 |
| S | O | $C_2H_5$ | $CHF_2$ | 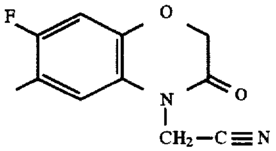 |
| S | O | $CH_3$ | $CF_3$ | 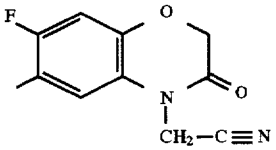 |
| S | O | $CHF_2$ | $C_2H_5$ | 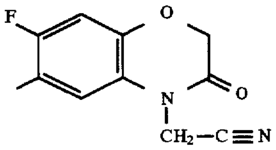 |
| S | O | $CHF_2$ | $CH_3$ | 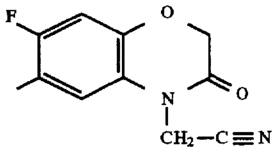 |
| S | O | 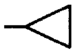 | $CHF_2$ | 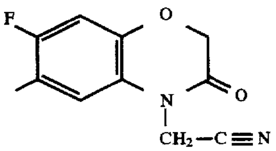 |
| S | O | 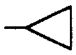 | $CH_3$ | 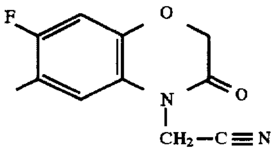 |
| S | O | $CH_3$ | 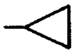 | 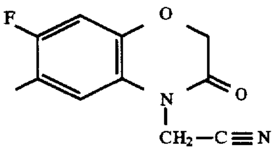 |
| S | O | n-$C_3H_7$ | $CHF_2$ | 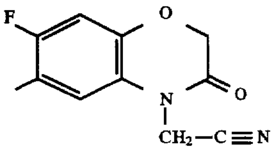 |
| S | O | n-$C_3H_7$ | $C_2H_5$ | 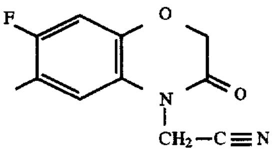 |

-continued
| A | Q | R | $R^2$ | Ar |
|---|---|---|---|---|
| S | O | $n\text{-}C_3H_7$ | $CH_3$ | 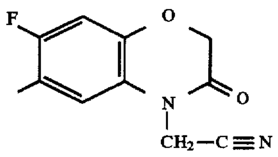 |
| S | O | $C_2H_5$ | $CH_2-C\equiv CH$ | 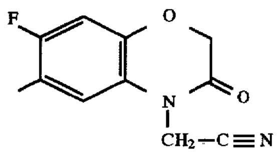 |
| S | O | $C_2H_5$ | $CH_2-CH=CH_2$ | 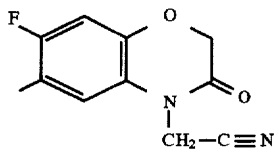 |
| S | O | $C_2H_5$ | $CH_2F$ | 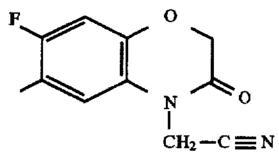 |
| S | O | $C_2H_5$ | $CH_3$ | 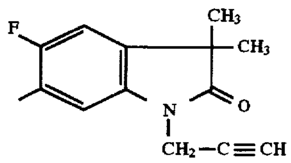 |
| S | O | $CH_3$ | $CH_2F$ | 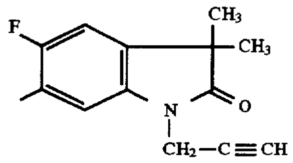 |
| S | O | $C_2H_5$ | $CHF_2$ | 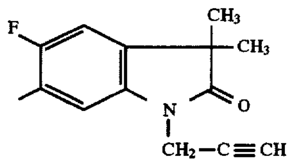 |
| S | O | $CH_3$ | $CF_3$ | 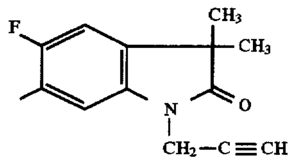 |
| S | O | $CHF_2$ | $C_2H_5$ | 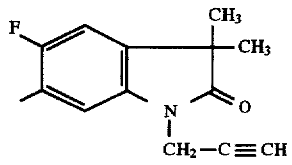 |

-continued
| A | Q | R | $R^2$ | Ar |
|---|---|---|---|---|
| S | O | $CHF_2$ | $CH_3$ | 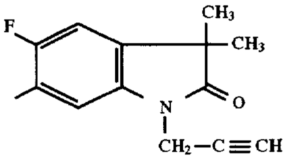 |
| S | O | 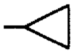 | $CHF_2$ | 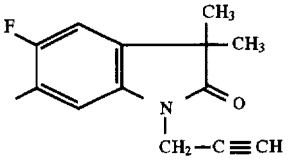 |
| S | O | 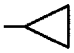 | $CH_3$ | 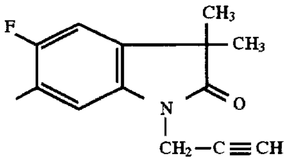 |
| S | O | $CH_3$ | 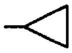 | 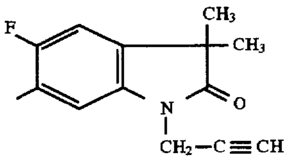 |
| S | O | n-$C_3H_7$ | $CHF_2$ | 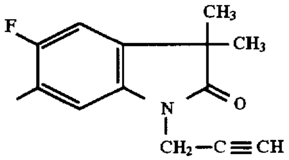 |
| S | O | n-$C_3H_7$ | $C_2H_5$ | 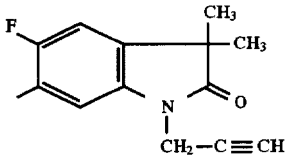 |
| S | O | n-$C_3H_7$ | $CH_3$ | 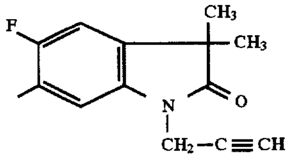 |
| S | O | $C_2H_5$ | $CH_2-C\equiv CH$ | 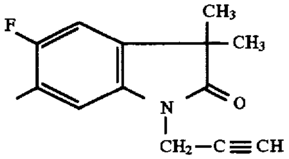 |
| S | O | $C_2H_5$ | $CH_2-C\equiv CH$ | 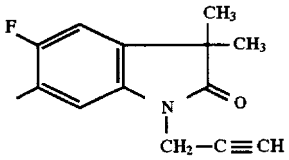 |

-continued
| A | Q | R | $R^2$ | Ar |
|---|---|---|---|---|
| S | O | $C_2H_5$ | $CH_2F$ | 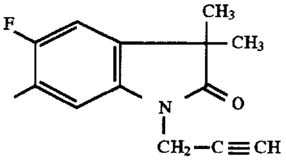 |
| S | O | $C_2H_5$ | $CH_3$ | 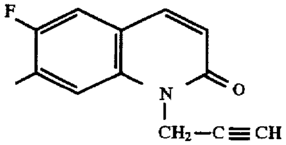 |
| S | O | $CH_3$ | $CH_2F$ | 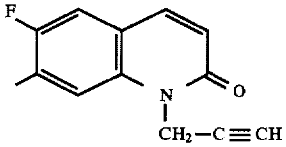 |
| S | O | $C_2H_5$ | $CHF_2$ | 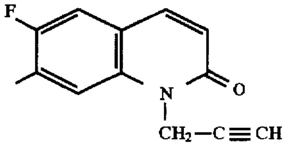 |
| S | O | $CH_3$ | $CF_3$ | 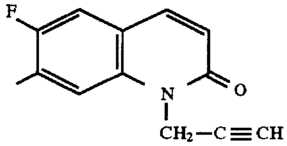 |
| S | O | $CHF_2$ | $C_2H_5$ | 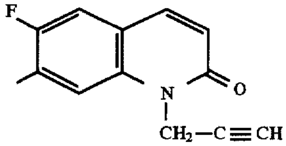 |
| S | O | $CHF_2$ | $CH_3$ | 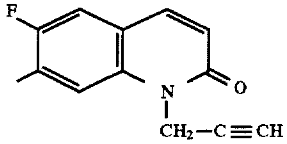 |
| S | O | 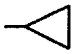 | $CHF_2$ | 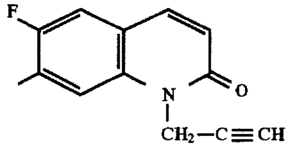 |
| S | O | 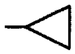 | $CH_3$ | 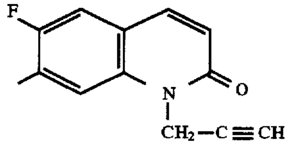 |
| S | O | $CH_3$ | 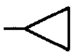 | 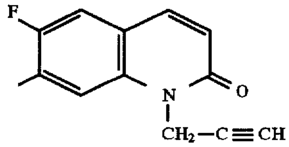 |

-continued
| A | Q | R | $R^2$ | Ar |
|---|---|---|---|---|
| S | O | n-$C_3H_7$ | $CHF_2$ | 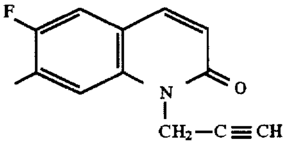 |
| S | O | n-$C_3H_7$ | $C_2H_5$ | 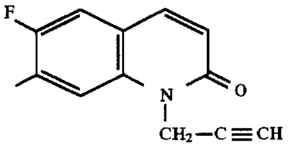 |
| S | O | n-$C_3H_7$ | $CH_3$ | 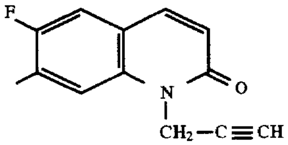 |
| S | O | $C_2H_5$ | $CH_2-C\equiv CH$ | 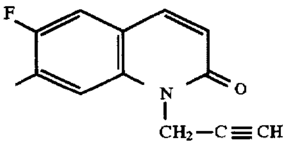 |
| S | O | $C_2H_5$ | $CH_2-C\equiv CH$ | 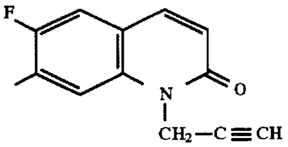 |
| S | O | $C_2H_5$ | $CH_2F$ | 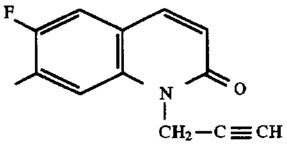 |
| S | O | $C_2H_5$ | $CH_3$ | 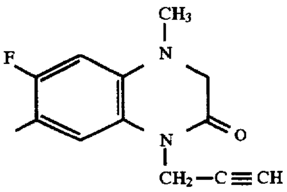 |
| S | O | $CH_3$ | $CH_2F$ | 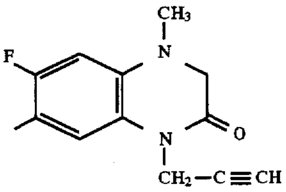 |
| S | O | $C_2H_5$ | $CHF_2$ | 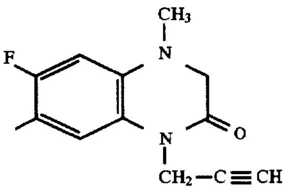 |

-continued
| A | Q | R | $R^2$ | Ar |
|---|---|---|---|---|
| S | O | $CH_3$ | $CF_3$ | 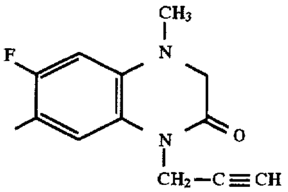 |
| S | O | $CHF_2$ | $C_2H_5$ | 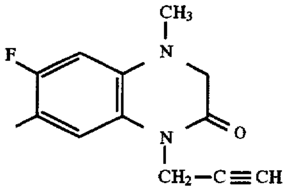 |
| S | O | $CHF_2$ | $CH_3$ | 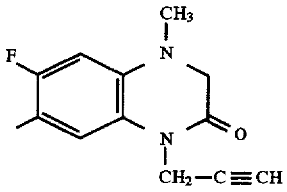 |
| S | O | 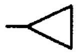 | $CHF_2$ | 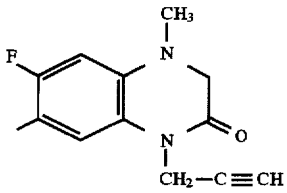 |
| S | O | 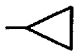 | $CH_3$ | 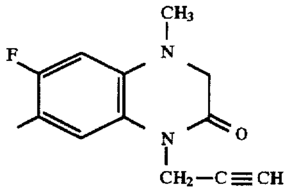 |
| S | O | $CH_3$ | 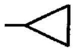 | 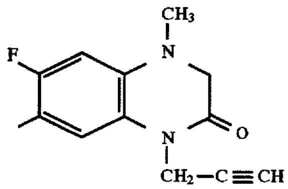 |
| S | O | n-$C_3H_7$ | $CHF_2$ | 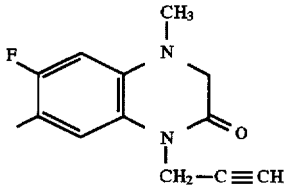 |
| S | O | n-$C_3H_7$ | $C_2H_5$ | 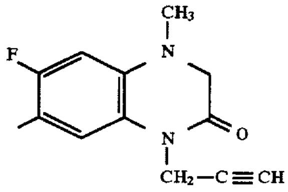 |

-continued
| A | Q | R | $R^2$ | Ar |
|---|---|---|---|---|
| S | O | $n\text{-}C_3H_7$ | $CH_3$ | 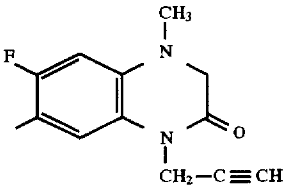 |
| S | O | $C_2H_5$ | $CH_2-C\equiv CH$ | 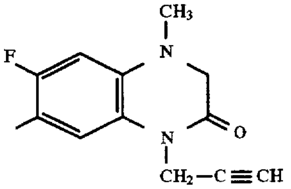 |
| S | O | $C_2H_5$ | $CH_2-CH=CH_2$ | 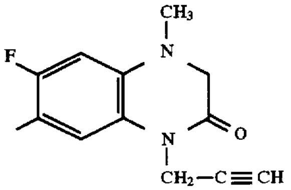 |
| S | 0 | $C_2H_5$ | $CH_2F$ | 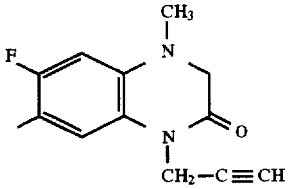 |
| S | O | $C_2H_5$ | $CH_3$ | 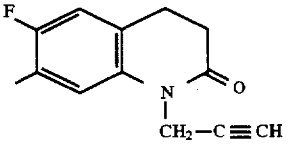 |
| S | O | $CH_3$ | $CH_2F$ | 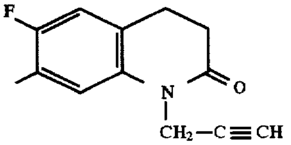 |
| S | O | $C_2H_5$ | $CHF_2$ | 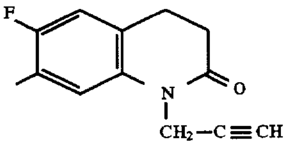 |
| S | O | $CH_3$ | $CF_3$ | 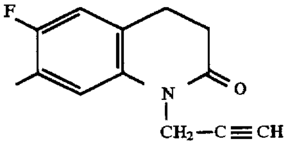 |
| S | O | $CHF_2$ | $C_2H_5$ | 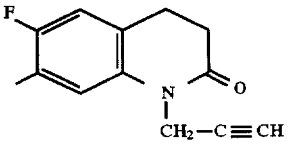 |

-continued
| A | Q | R | $R^2$ | Ar |
|---|---|---|---|---|
| S | O | $CHF_2$ | $CH_3$ | 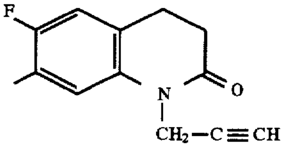 |
| S | O | 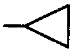 | $CHF_2$ | 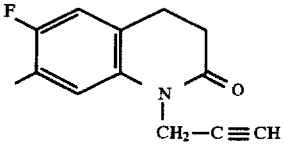 |
| S | O | 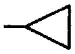 | $CH_3$ | 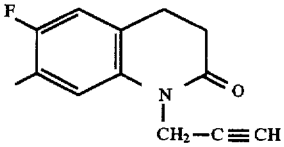 |
| S | O | $CH_3$ | 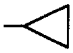 | 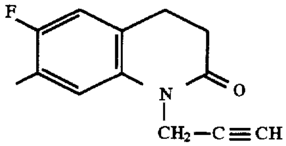 |
| S | O | n-$C_3H_7$ | $CHF_2$ | 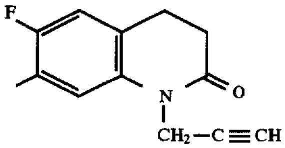 |
| S | O | n-$C_3H_7$ | $C_2H_5$ | 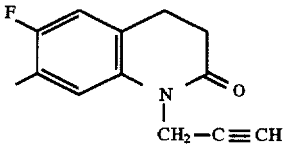 |
| S | O | n-$C_3H_7$ | $CH_3$ | 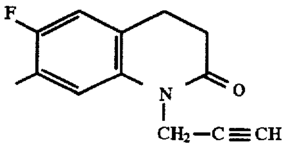 |
| S | O | $C_2H_5$ | $CH_2-C\equiv CH$ | 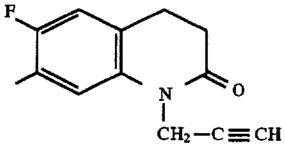 |
| S | O | $C_2H_5$ | $CH_2-C\equiv CH$ | 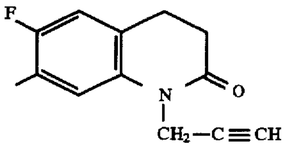 |
| S | O | $C_2H_5$ | $CH_2F$ | 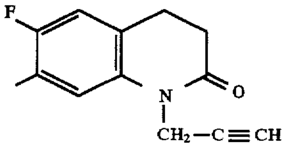 |

-continued
| A | Q | R | $R^2$ | Ar |
|---|---|---|---|---|
| S | O | $CH_3$ | $CH_3$ | 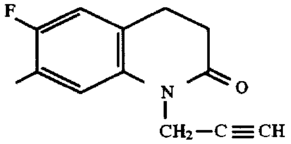 |
| S | O | $CH_3$ | $C_2H_5$ | 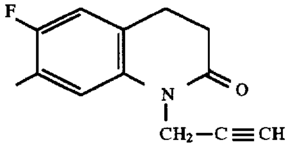 |
| S | O | $CH_3$ | $CH_2-CH=CH_2$ | 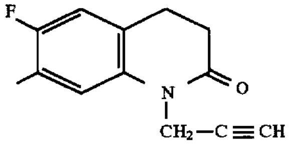 |
| S | O | $CH_3$ | $CH_2-C\equiv CH$ | 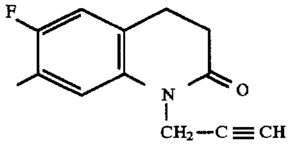 |
| S | O | $CH_3$ | $CHF_2$ | 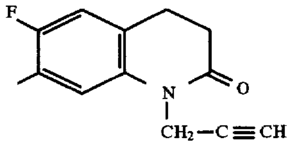 |
| S | O | $C_2H_5$ | $C_2H_5$ | 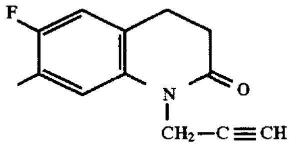 |
| S | O | $CH_3$ | $CH_2F$ | 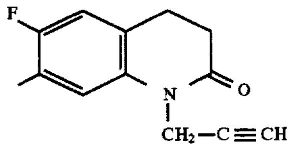 |
| S | O | $CH_3$ | $CF_3$ | 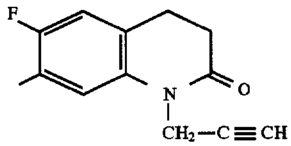 |
| S | O | $CH_3$ | $CH_3$ | 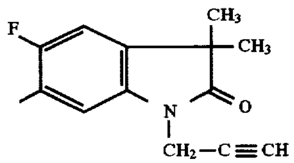 |
| S | O | $CH_3$ | $C_2H_5$ | 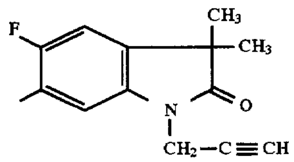 |

-continued
| A | Q | R | $R^2$ | Ar |
| --- | --- | --- | --- | --- |
| S | O | $CH_3$ | $CH_2-CH=CH_2$ | 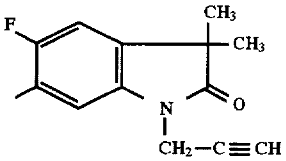 |
| S | O | $CH_3$ | $CH_2-C\equiv CH$ | 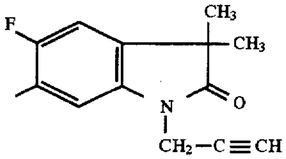 |
| S | O | $CH_3$ | $CHF_2$ | 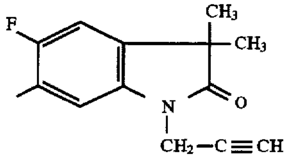 |
| S | O | $C_2H_5$ | $C_2H_5$ | 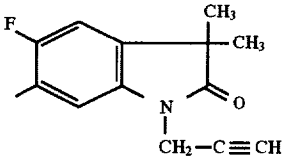 |
| S | O | $CH_3$ | $CH_2F$ | 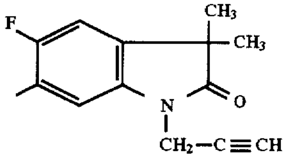 |
| S | O | $CH_3$ | $CF_3$ | 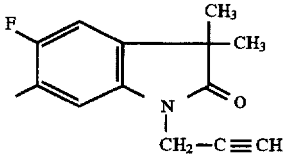 |
| S | O | $CH_3$ | $CH_3$ | 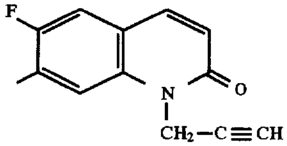 |
| S | O | $CH_3$ | $C_2H_5$ | 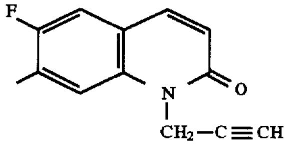 |
| S | O | $CH_3$ | $CH_2-CH=CH_2$ | 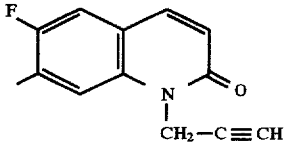 |

-continued
| A | Q | R | $R^2$ | Ar |
|---|---|---|---|---|
| S | O | $CH_3$ | $CH_2-C\equiv CH$ | 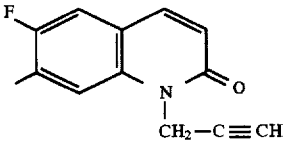 |
| S | O | $CH_3$ | $CHF_2$ | 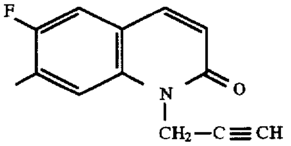 |
| S | O | $C_2H_5$ | $C_2H_5$ | 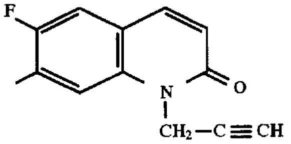 |
| S | O | $CH_3$ | $CH_2F$ | 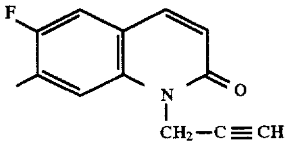 |
| S | O | $CH_3$ | $CF_3$ | 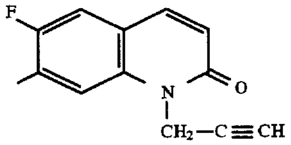 |
| S | O | $CH_3$ | $CH_3$ | 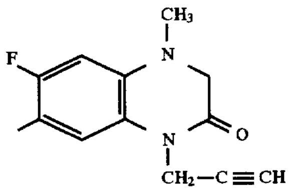 |
| S | O | $CH_3$ | $C_2H_5$ | 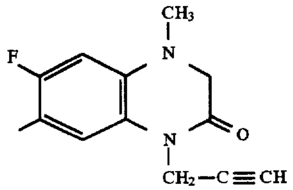 |
| S | O | $CH_3$ | $CH_2-CH=CH_2$ | 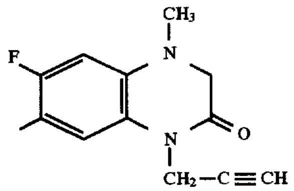 |
| S | O | $CH_3$ | $CH_2-C\equiv CH$ | 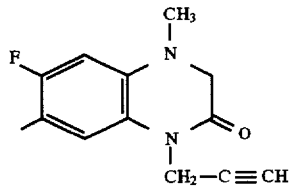 |

-continued
| A | Q | R | $R^2$ | Ar |
|---|---|---|---|---|
| S | O | $CH_3$ | $CHF_2$ | 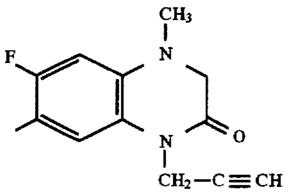 |
| S | O | $C_2H_5$ | $C_2H_5$ | 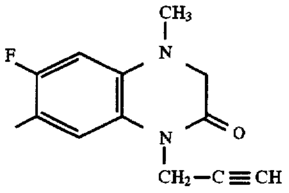 |
| S | O | $CH_3$ | $CH_2F$ | 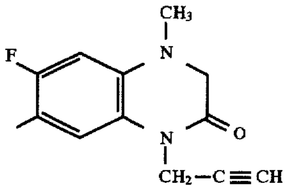 |
| S | O | $CH_3$ | $CF_3$ | 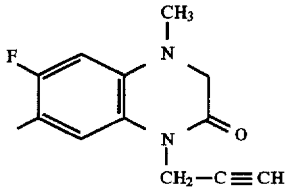 |
| S | O | $CH_3$ | $CH_3$ | 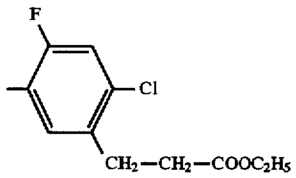 |
| S | O | $CH_3$ | $C_2H_5$ | 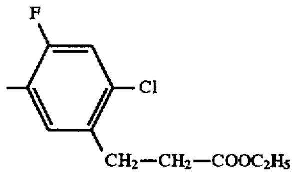 |
| S | O | $CH_3$ | $CH_2-CH=CH_2$ | 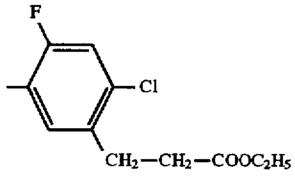 |
| S | O | $CH_3$ | $CH_2-C\equiv CH$ | 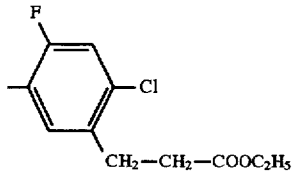 |

-continued
| A | Q | R | $R^2$ | Ar |
|---|---|---|---|---|
| S | O | $CH_3$ | $CHF_2$ | 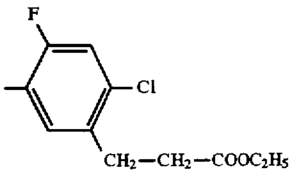 |
| S | O | $C_2H_5$ | $C_2H_5$ | 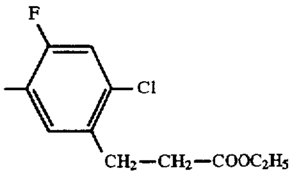 |
| S | O | $CH_3$ | $CH_2F$ | 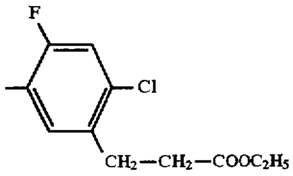 |
| S | O | $CH_3$ | $CF_3$ | 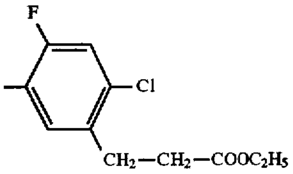 |
| S | O | $CH_3$ | $CH_3$ | 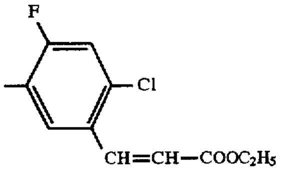 |
| S | O | $CH_3$ | $C_2H_5$ | 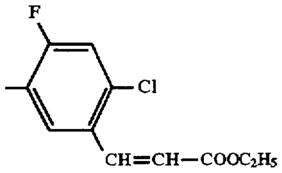 |
| S | O | $CH_3$ | $CH_2-CH=CH_2$ | 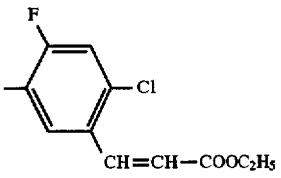 |
| S | O | $CH_3$ | $CH_2-C\equiv CH$ | 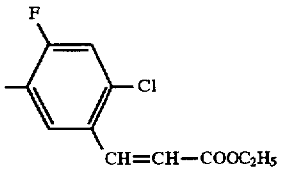 |

-continued
| A | Q | R | $R^2$ | Ar |
|---|---|---|---|---|
| S | O | $CH_3$ | $CHF_2$ | 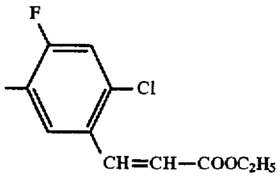 |
| S | O | $C_2H_5$ | $C_2H_5$ | 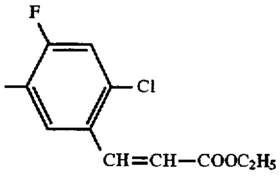 |
| S | O | $CH_3$ | $CH_2F$ | 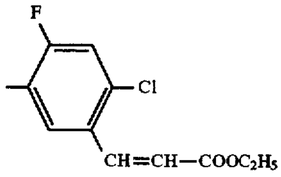 |
| S | O | $CH_3$ | $CF_3$ | 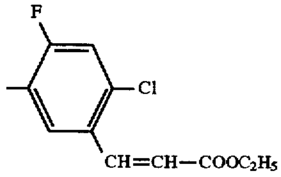 |
| S | O | $CH_3$ | $CH_3$ | 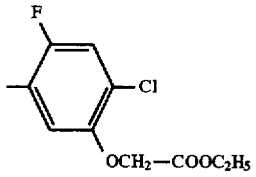 |
| S | O | $CH_3$ | $C_2H_5$ | 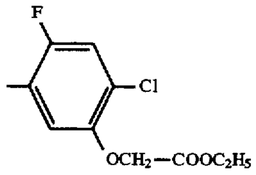 |
| S | O | $CH_3$ | $CH_2-CH=CH_2$ | 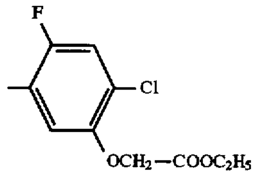 |
| S | O | $CH_3$ | $CH_2-C\equiv CH$ | 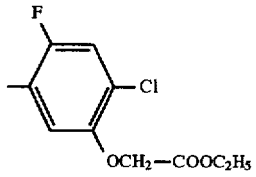 |

-continued
| A | Q | R | $R^2$ | Ar |
|---|---|---|---|---|
| S | O | $CH_3$ | $CHF_2$ | 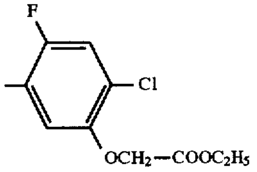 |
| S | O | $C_2H_5$ | $C_2H_5$ | 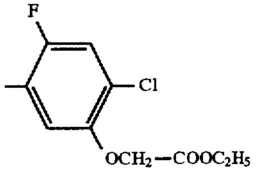 |
| S | O | $CH_3$ | $CH_2F$ | 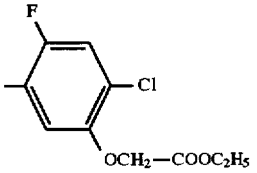 |
| S | O | $CH_3$ | $CF_3$ | 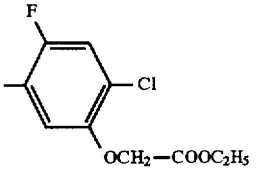 |
| S | O | $CH_3$ | $CH_3$ | 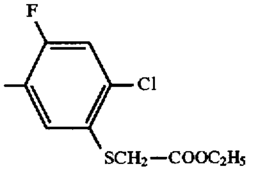 |
| S | O | $CH_3$ | $C_2H_5$ | 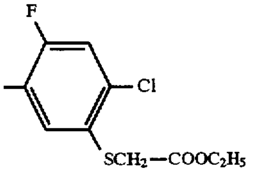 |
| S | O | $CH_3$ | $CH_2-CH=CH_2$ | 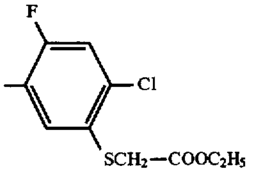 |
| S | O | $CH_3$ | $CH_2-C\equiv CH$ | 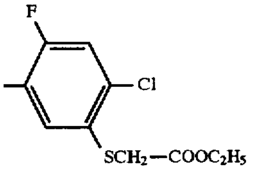 |

-continued
| A | Q | R | $R^2$ | Ar |
|---|---|---|---|---|
| S | O | $CH_3$ | $CHF_2$ | 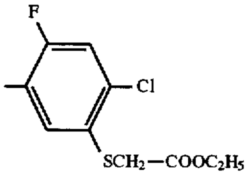 |
| S | O | $C_2H_5$ | $C_2H_5$ | 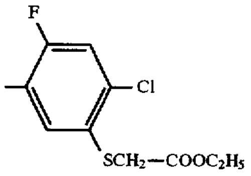 |
| S | O | $CH_3$ | $CH_2F$ | 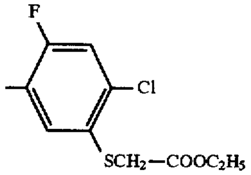 |
| S | O | $CH_3$ | $CF_3$ | 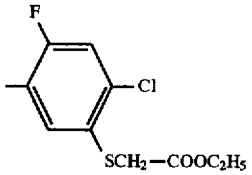 |
| S | O | $CH_3$ | $CH_3$ | 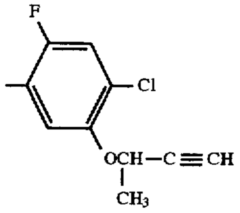 |
| S | O | $CH_3$ | $C_2H_5$ | 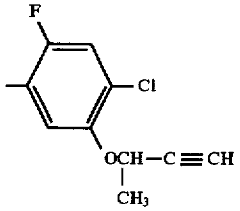 |
| S | O | $CH_3$ | $CH_2-CH=CH_2$ | 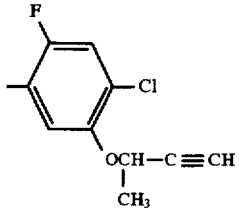 |
| S | O | $CH_3$ | $CH_2-C\equiv CH$ | 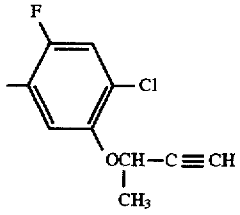 |

-continued
| A | Q | R | $R^2$ | Ar |
|---|---|---|---|---|
| S | O | $CH_3$ | $CHF_2$ | 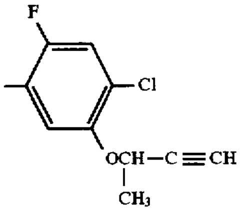 |
| S | O | $C_2H_5$ | $C_2H_5$ | 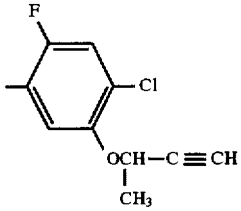 |
| S | O | $CH_3$ | $CH_2F$ | 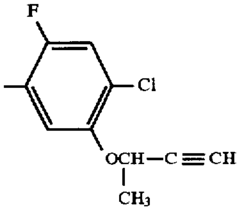 |
| S | O | $CH_3$ | $CF_3$ | 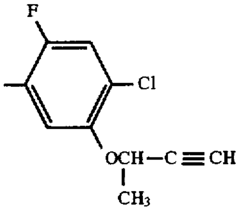 |
| S | O | $CH_3$ | $CH_3$ | 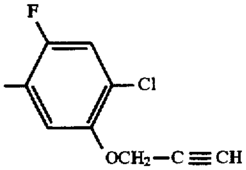 |
| S | O | $CH_3$ | $C_2H_5$ | 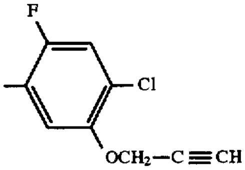 |
| S | O | $CH_3$ | $CH_2-CH=CH_2$ | 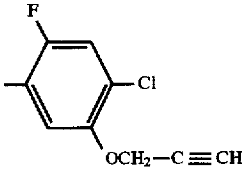 |
| S | O | $CH_3$ | $CH_2-C\equiv CH$ | 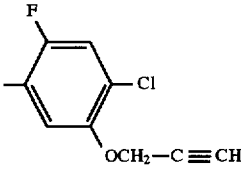 |

-continued
| A | Q | R | $R^2$ | Ar |
|---|---|---|---|---|
| S | O | $CH_3$ | $CHF_2$ | 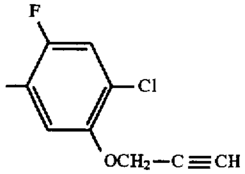 |
| S | O | $C_2H_5$ | $C_2H_5$ | 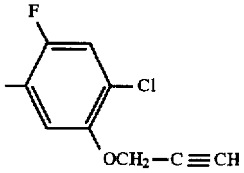 |
| S | O | $CH_3$ | $CH_2F$ | 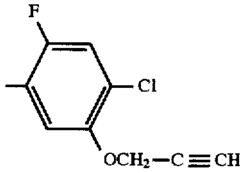 |
| S | O | $CH_3$ | $CF_3$ | 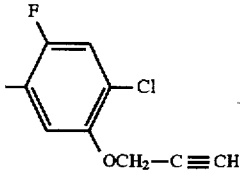 |
| S | O | $CH_3$ | $CH_3$ | 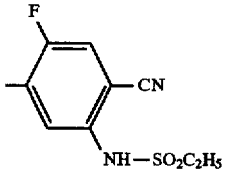 |
| S | O | $CH_3$ | $C_2H_5$ | 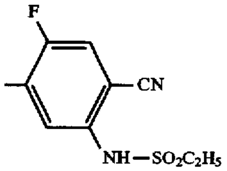 |
| S | O | $CH_3$ | $CH_2-CH=CH_2$ | 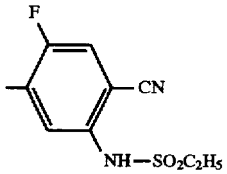 |
| S | O | $CH_3$ | $CH_2-C\equiv CH$ | 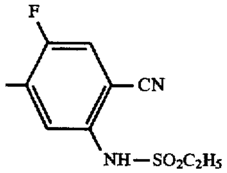 |

-continued
| A | Q | R | $R^2$ | Ar |
|---|---|---|---|---|
| S | O | $CH_3$ | $CHF_2$ | 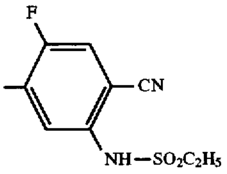 |
| S | O | $C_2H_5$ | $C_2H_5$ | 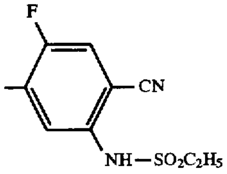 |
| S | O | $CH_3$ | $CH_2F$ | 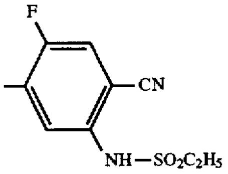 |
| S | O | $CH_3$ | $CF_3$ | 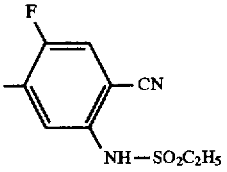 |
| S | O | $CH_3$ | $CH_3$ | 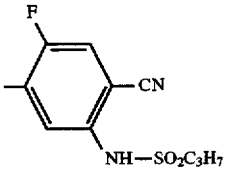 |
| S | O | $CH_3$ | $C_2H_5$ | 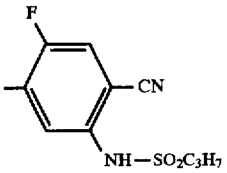 |
| S | O | $CH_3$ | $CH_2-CH=CH_2$ | 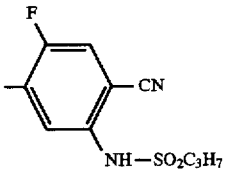 |
| S | O | $CH_3$ | $CH_2-C\equiv CH$ | 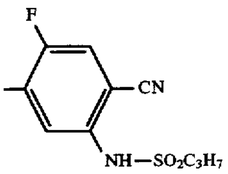 |

-continued
| A | Q | R | $R^2$ | Ar |
|---|---|---|---|---|
| S | O | $CH_3$ | $CHF_2$ | 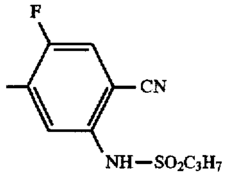 |
| S | O | $C_2H_5$ | $C_2H_5$ | 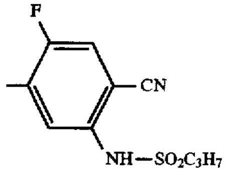 |
| S | O | $CH_3$ | $CH_2F$ | 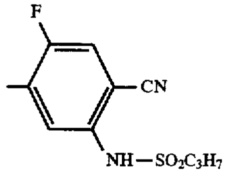 |
| S | O | $CH_3$ | $CF_3$ | 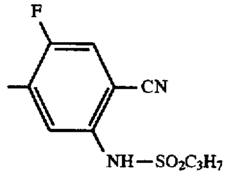 |
| S | O | $C_2H_5$ | $CH_3$ | 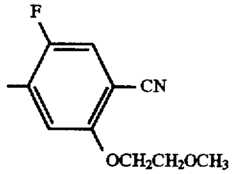 |
| S | O | $CH_3$ | $CH_2F$ | 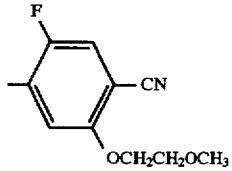 |
| S | O | $C_2H_5$ | $CHF_2$ | 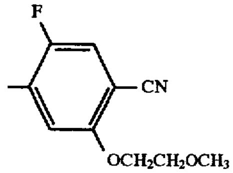 |
| S | O | $CH_3$ | $CF_3$ | 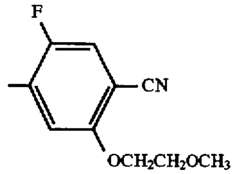 |

-continued
| A | Q | R | $R^2$ | Ar |
|---|---|---|---|---|
| S | O | $CHF_2$ | $C_2H_5$ | 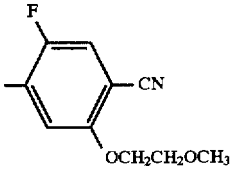 |
| S | O | $CHF_2$ | $CH_3$ | 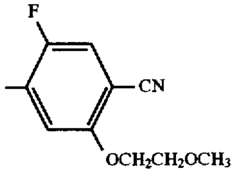 |
| S | O | 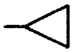 | $CHF_2$ | 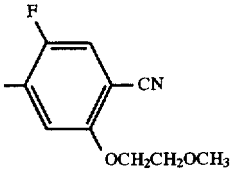 |
| S | O | 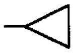 | $CH_3$ | 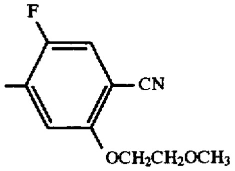 |
| S | O | $CH_3$ | 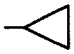 | 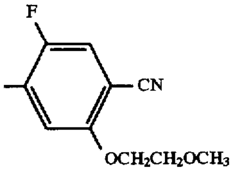 |
| S | O | n-$C_3H_7$ | $CHF_2$ | 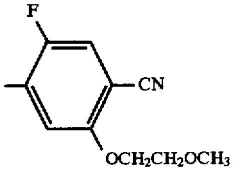 |
| S | O | n-$C_3H_7$ | $C_2H_5$ | 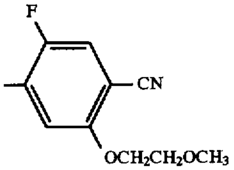 |
| S | O | n-$C_3H_7$ | $CH_3$ | 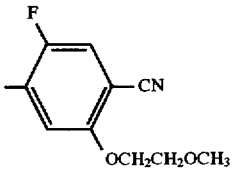 |

-continued
| A | Q | R | $R^2$ | Ar |
|---|---|---|---|---|
| S | O | $C_2H_5$ | $CH_2-C\equiv CH$ | 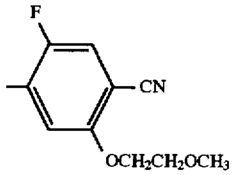 |
| S | O | $C_2H_5$ | $CH_2-C\equiv CH$ | 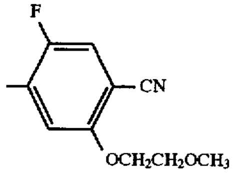 |
| S | O | $C_2H_5$ | $CH_2F$ | 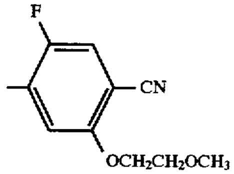 |
| S | O | $C_2H_5$ | $CH_3$ | 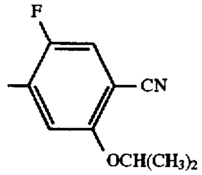 |
| S | O | $CH_3$ | $CH_2F$ | 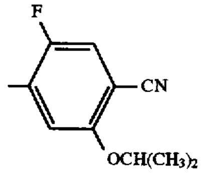 |
| S | O | $C_2H_5$ | $CHF_2$ | 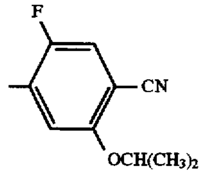 |
| S | O | $CH_3$ | $CF_3$ | 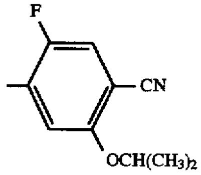 |
| S | O | $CHF_2$ | $C_2H_5$ | 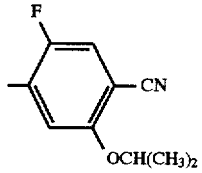 |

-continued
| A | Q | R | $R^2$ | Ar |
|---|---|---|---|---|
| S | O | $CHF_2$ | $CH_3$ | 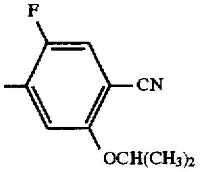 |
| S | O | 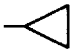 | $CHF_2$ | 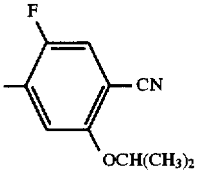 |
| S | O | 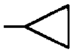 | $CH_3$ | 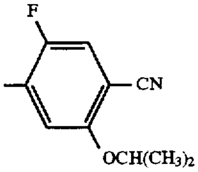 |
| S | O | $CH_3$ | 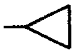 | 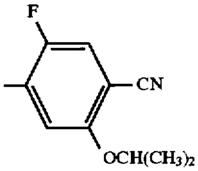 |
| S | O | n-$C_3H_7$ | $CHF_2$ | 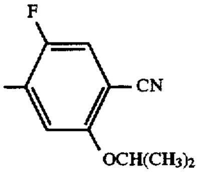 |
| S | O | n-$C_3H_7$ | $C_2H_5$ | 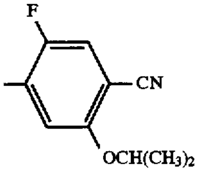 |
| S | O | n-$C_3H_7$ | $CH_3$ | 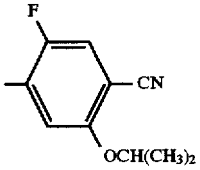 |
| S | O | $C_2H_5$ | $CH_2—C≡CH$ | 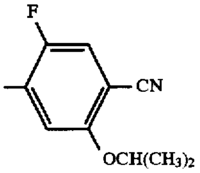 |

-continued
| A | Q | R | $R^2$ | Ar |
|---|---|---|---|---|
| S | O | $C_2H_5$ | $CH_2-C\equiv CH$ | 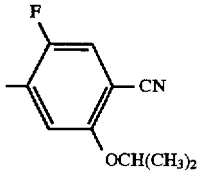 |
| S | O | $C_2H_5$ | $CH_2F$ | 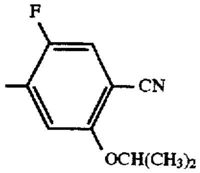 |
| S | O | $CH_3$ | $CH_3$ | 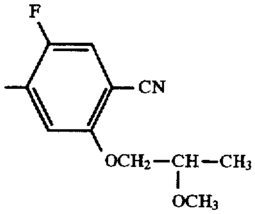 |
| S | O | $CH_3$ | $C_2H_5$ | 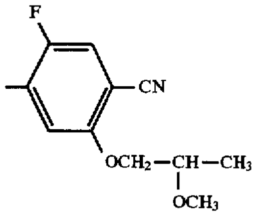 |
| S | O | $CH_3$ | $CH_2-CH=CH_2$ | 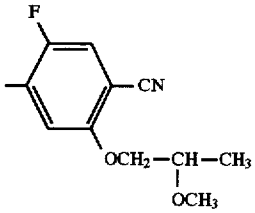 |
| S | O | $CH_3$ | $CH_2-C\equiv CH$ | 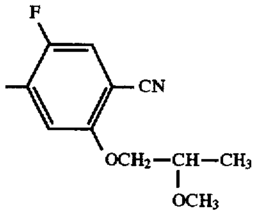 |
| S | O | $CH_3$ | $CHF_2$ | 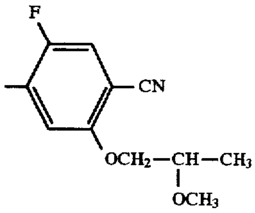 |

-continued
| A | Q | R | $R^2$ | Ar |
|---|---|---|---|---|
| S | O | $C_2H_5$ | $C_2H_5$ | 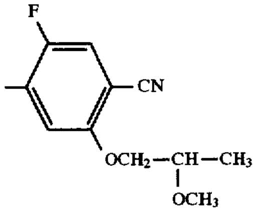 |
| S | O | $CH_3$ | $CH_2F$ | 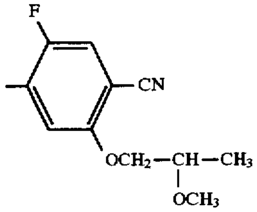 |
| S | O | $CH_3$ | $CF_3$ | 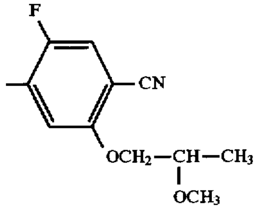 |
| S | O | $CH_3$ | $CH_3$ | 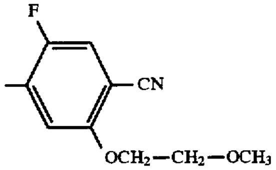 |
| S | O | $CH_3$ | $C_2H_5$ | 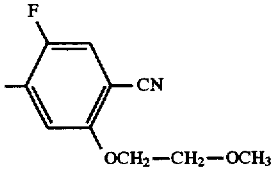 |
| S | O | $CH_3$ | $CH_2-CH=CH_2$ | 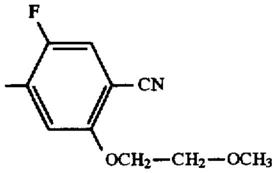 |
| S | O | $CH_3$ | $CH_2-C\equiv CH$ | 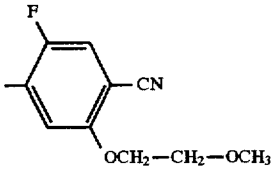 |
| S | O | $CH_3$ | $CHF_2$ | 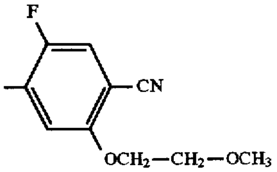 |

-continued

| A | Q | R | $R^2$ | Ar |
|---|---|---|---|---|
| S | O | $C_2H_5$ | $C_2H_5$ | 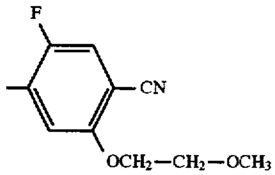 |
| S | O | $CH_3$ | $CH_2F$ | 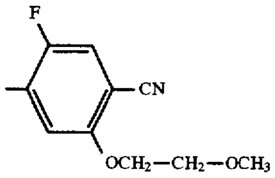 |
| S | O | $CH_3$ | $CF_3$ | 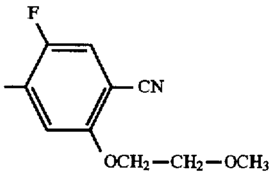 |

If, for example, 4-(4-chloro-2-fluoro-5-methoxy-phenyl) -2-methyl-thio-semicarbazide and phosgene are used as starting materials and chlorodifluoromethane as alkylating agent in the subsequent step, the course of the reaction in the process according to the invention can be outlined as follows:

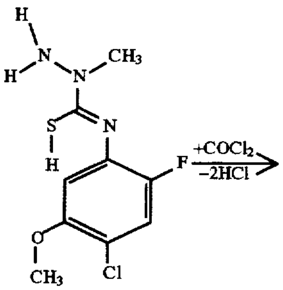

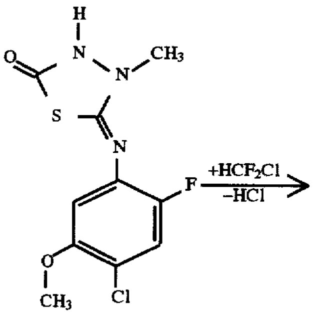

-continued

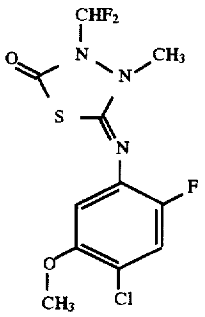

Formula (II) provides a general definition of the arylimino compounds to be used as starting materials in the process according to the invention for the preparation of the compounds of the general formula (I). In formula (II), A, R, $R^2$ and Ar preferably, or in particular, have those meanings which have already been mentioned above in connection with the description of the compounds of the formula (I) as being preferred, or particularly preferred, for A, R, $R^2$ and Ar.

The starting materials of the formula (II) have been disclosed and/or can be prepared by known processes (cf. EP-A 258182, U.S. Pat. No. 4,721,522, DE-A 3722074, U.S. Pat. No. 5,108,486, preparation examples).

Formula (III) provides a general definition of the reactive carbonic acid derivatives to be furthermore used as starting materials in the process according to the invention for the preparation of the compounds of the general formula (I). In formula (III), Q preferably, or in particular, has that meaning which has already been mentioned above in connection with the description of the compounds of the formula (I) as being preferred, or particularly preferred, for Q; X preferably represents fluorine, chlorine, bromine, $C_1$–$C_4$-alkoxy, phenoxy or benzyloxy, in particular chlorine, methoxy or phenoxy.

The starting materials of the formula (III) are known chemicals for synthesis.

Formula (IV) provides a general definition of the alkylating agents which, if appropriate, are also to be used as starting materials in the process according to the invention for the preparation of the compounds of the general formula (I). In formula (IV), $R^2$ preferably, or in particular, has that meaning which has already been mentioned above in connection with the description of the compounds of the formula (I) as being preferred, or particularly preferred, for $R^2$; $X^1$ preferably represents chlorine, bromine, iodine or the group $—O—SO_2—O—R^2$.

The starting materials of the formula (IV) are known chemicals for synthesis.

Diluents which are suitable for carrying out the process according to the invention are the customary organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, tetrachloromethane; ethers, such as diethyl ether, diisopropyl ether, dioxane, tetrahydrofuran, ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methyl-pyrrolidone or hexamethylphosphoric triamide; esters, such as methyl acetate or ethyl acetate, sulphoxides, such as dimethyl sulphoxide, alcohols such as methanol, ethanol, n- or i-propanol, ethylene glycol monomethyl ether, ethylene glycol monoethyl ether, diethylene glycol monomethyl ether, diethylene glycol monoethyl ether, mixtures of these with water, or pure water.

The process according to the invention is preferably carried out in the presence of a suitable reaction auxiliary. The suitable substances are all customary inorganic or organic bases. These include, for example, the hydrides, hydroxides, amides, alcoholates, acetates, carbonates or hydrogen carbonates of alkali metals or alkaline earth metals, such as, for example, lithium hydride, sodium hydride, potassium hydride or calcium hydride, lithium amide, sodium amide or calcium amide, sodium methylate or potassium methylate, sodium ethylate or potassium ethylate, sodium propylate or potassium propylate, aluminium isopropylate, sodium tert-butylate or potassium tert-butylate, sodium hydroxide or potassium hydroxide, ammonium hydroxide, sodium acetate, potassium acetate or calcium acetate, ammonium acetate, sodium carbonate, potassium carbonate or calcium carbonate, ammonium carbonate, sodium hydrogen carbonate or potassium hydrogen carbonate, and basic organic nitrogen compounds, such as trimethylamine, triethylamine, tripropylamine, tributylamine, ethyl-diisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl- and 4methylpyridine, 2,4-dimethyl-, 2,6-dimethyl-, 3,4-dimethyl- and 3,5-dimethyl-pyridine, 5-ethyl-2-methyl-pyridine, N-methylpiperidine, N,N-dimethylaminopyridine, diazabicyclooctane (DABCO), diazabicyclononene (DBN) or diazabicycloundecene (DBU).

When carrying out the process according to the invention, the reaction temperatures can be varied within a substantial range. In general, the process is carried out at temperatures between −10 C. and +150 C., preferably at temperatures between 0 C. and 100 C., in particular at temperatures between 10° C. and 80° C. In general, the process according to the invention is carried out under atmospheric pressure. However, it is also possible to carry out the process under elevated or reduced pressure, in general between 0.1 bar and 10 bar.

To carry out the process according to the invention, the starting materials required in each case are generally employed in approximately equimolar amounts. However, it is also possible to use one of the two components employed in each case in a larger excess. In general, the reactions are carried out in a suitable diluent, if appropriate in the presence of a reaction auxiliary, and the reaction mixture is stirred for several hours at the temperature required in each case. Working-up in the process according to the invention is carried out in each case by customary methods (cf. the preparation examples).

The active compounds according to the invention can be used as defoliants, desiccants, haulm killers and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

Depending on the concentration, the compounds are suitable for total weed control, for example on industrial terrain and rail tracks, and on paths and areas with or without tree stands. Equally, the compounds can be employed for controlling weeds in perennial crops, for example forests, ornamental tree plantations, orchards, vineyards, citrus groves, nut orchards, banana plantations, coffee plantations, tea plantations, rubber plantations, oil palm plantations, cocoa plantations, soft fruit plantations and hopfields, in lawns, turf and pastures, and for selective weed control in annual crops.

The compounds of the formula (I) according to the invention are particularly suitable for selectively controlling monocotyledon and dicotyledon weeds in monocotyledon and dicotyledon crops, both pre- and post-emergence.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, organic solvents can, for example, also be used as auxiliary solvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are: for example ammonium salts and ground natural minerals such as kaolins, clays, talc, chalk quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Adhesives such as carboxymethylcellulose and natural and synthetic polymers in the form of powders, granules or latexes such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, ready mixes or tank mixes being possible Possible components for the mixtures are known herbicides, such as, for example, anilides, such as, for example, diflufenican and propanil; arylcarboxylic acids, such as, for example, dichloropicolinic acid, dicamba and picloram; aryloxyalkanoic acids, such as, for example, 2,4 D, 2,4 DB, 2,4 DP, fluroxypyr, MCPA, MCPP and triclopyr; aryloxy-phenoxy-alkanoic esters, such as, for example, diclofop-methyl, fenoxapropethyl, fluazifop-butyl, haloxyfop-methyl and quizalofop-ethyl; azinones, such as, for example, chloridazon and norflurazon; carbamates, such as, for example, chlorpropham, desmedipham, phenmedipham and propham; chloracetanilides, such as, for example, alachlor, acetochlor, butachlor, metazachlor, metolachlor, pretilachlor and propachlor; dinitroanilines, such as, for example, oryzalin, pendimethalin and trifluralin; diphenyl ethers, such as, for example, acifluorfen, bifenox, fluoroglycofen, fomesafen, halosafen, lactofen and oxyfluorfen; ureas, such as, for example, chlortoluron, diuron, fluometuron, isoproturon, linuron and methabenzthiazuron; hydroxylamines, such as, for example, alloxydim, clethodim, cycloxydim, sethoxydim and tralkoxydim; imidazolinones, such as, for example, imazethapyr, imazamethabenz, imazapyr and imazaquin; nitriles, such as, for example, bromoxynil, dichlobenil and ioxynil; oxyacetamides, such as, for example, mefenacet; sulphonylureas, such as, for example, amidosulfuron, bensulfuron-methyl, chlorimuron-ethyl, chlorsulfuron, cinosulfuron, metsulfuron-methyl, nicosulfuron, primisulfuron, pyrazosulftiron-ethyl, thifensulfuron-methyl, triasulfuron and tribenuron-methyl; thiolcarbamates, such as, for example, butylate, cycloate, diallate, EPTC, esprocarb, molinate, prosulfocarb, thiobencarb and triallate; triazines, such as, for example, atrazine, cyanazine, simazine, simetryn, tertbutryn and terbutylazine; triazinones, such as, for example, hexazinon, metamitron and metribuzin; others, such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds such as fungicides, insecticides, acaricides, nematicides, bird repellants, plant nutrients and soil conditioners, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or spreading.

The active compounds according to the invention can be applied either before or after emergence of the plants. They can also be incorporated into the soil before sowing.

The amount of active compound used can vary within a substantial range. It depends essentially on the nature of the desired effect. In general, the rates are between 10 g and 10 kg of active compound per hectare of soil surface, preferably between 50 g and 5 kg per ha.

The preparation and use of the active compounds according to the invention can be seen from the examples which follow.

Preparation Examples

EXAMPLE 1

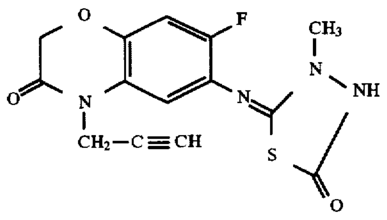

A suspension of 3.1 g (10 mMol) of 2-methyl-4-(7-fluoro-3,4-dihydro-3-oxo-4-propargyl-(2H)-1,4-benzoxazin-6-yl)-thiosemicarbazide in 50 ml of dichloromethane is treated at approximately 20 C. with 6 g (12 mMol) of a 20% strength solution of phosgene in toluene. The reaction mixture is heated for approximately 15 hours at 40 C., the solvent is removed in vacuo, and the residue is taken up in water. The mixture is rendered neutral using sodium bicarbonate solution, and the solid is filtered off, washed with water and dried in vacuo at 40–50 C.

This gives 2.8 g (84% of theory) of 2-(7-fluoro-3,4-dihydro-3-oxo-4-propargyl-(2H)-1,4-benzoxazin-6-yl-imino)-3-methyl-3,4-dihydro-5-oxo-(4H)-1,3,4-thiadiazole. Melting point: 214 C.

EXAMPLE 2

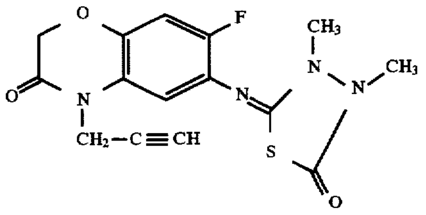

A mixture of 1.7 g (5 mMol) of 2-(7-fluoro-3,4-dihydro-3-oxo-4-propargyl-(2H)-1,4-benzoxazin-6yl-imino)-3-methyl-3,4-dihydro-5-oxo-(4H)-1,3,4-thiadiazole, 1.4 g (10 mMol) of potassium carbonate and 50 ml of acetonitrile is treated with 1.1 g (7.5 mMol) of methyl iodide. The reaction mixture is heated for 5 hours at 40 C. The solvent is removed in vacuo, the residue is taken up in water, and the mixture is rendered neutral and extracted using dichloromethane. The organic phase is dried over magnesium sulphate, concentrated and purified by chromatography (eluent: dichloromethane/methanol: 40:1).

This gives 0.75 g (42% of theory) of 3,4-dimethyl-2-(7-fluoro-3,4-dihydro-3-oxo-4-propargyl-(2)-1,4-benzoxazin-6-yl-imino)-3,4-dihydro-5-oxo-1,3,4-thiadiazole. Melting point: 104 C.

EXAMPLE 3

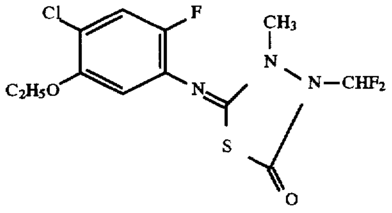

A solution of 3.3 g (11 mMol) of 2-(4-chloro-2-fluoro-5-ethoxy-phenyl-imino)-3-methyl-3,4-dihydro-5-oxo-(4H)-1,3,4-thiadiazole in 80 ml of dimethylformamide is treated with 3.4 g (24 mMol) of potassium carbonate, and chlorodifluoromethane is slowly passed in at 60 C. in the course of 6 hours. After the reaction has ended, most of the solvent is removed in vacuo. The oily residue is taken up in water, and the mixture is rendered neutral using hydrochloric acid and extracted using dichloromethane. The organic phase is dried over magnesium sulphate, concentrated and separated by chromatography using dichloromethane as the eluent.

The first fraction obtained is 0.4 g of 2-(4-chloro-2-fluoro-5-ethoxyphenylimino)-4-difluoromethyl-3-methyl-3,4-dihydro-5-oxo-1,3,4-thiadiazole. Melting point: 121 C.

The second fraction obtained is 0.5 g of 2-(4-chloro-2-fluoro-5-ethoxyphenylimino)-3-methyl-5-difluoromethoxy-1,3,4-thiadiazole. Melting point: 42 C.

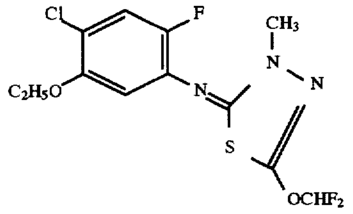

The compound listed as Example 45 in Table 1 can be prepared for example as follows:

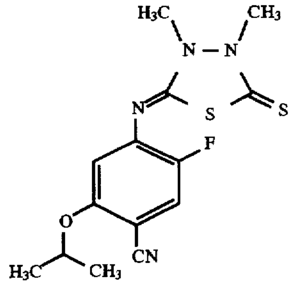

A solution of 1.7 g (5.7 mMol) of 4-(4-cyano-2-fluoro-5-i-propoxy-phenyl)-1,2-dimethylthiosemicarbazide in 30 ml of dry dichloromethane is treated with 0.66 g (5.7 mMol) of thiophosgene. The reaction is slightly exothermic. The reaction mixture is stirred for 4 hours at reflux temperature, the solvent is removed in vacuo, and the residue is stirred with saturated sodium bicarbonate solution. The solid formed is filtered off with suction, washed with water and pressed on a porous plate.

This gives 1.5 g (78% of theory) of 2-(4-cyano-2-fluoro-5-i-propoxy-phenylimino)-3,4-dimethyl-5-thio-1,3,4-thiadiazole of melting point 117 C.

Other examples of the compounds of the formula (I)—or of the formulae (1A) and (1B)—which can be prepared analogously to Examples 1 to 3 and following the general description of the preparation process according to the invention are those listed in Table 1 below.

TABLE 1

Examples of the compounds of the formula (I)

| Ex. No. | Gen. formula | Ar | R | $R^2$ | Q | A | Melting point (C.) |
|---|---|---|---|---|---|---|---|
| 4 | IA | 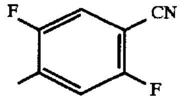 | $CH_3$ | $CH_3$ | O | S | 118 |
| 5 | IA | 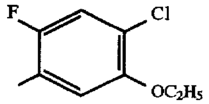 | $CH_3$ | $C_2H_5$ | O | S | 95 |
| 6 | IA | 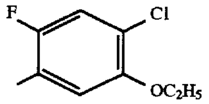 | $CH_3$ | $CH_3$ | O | S | 103 |
| 7 | IA | 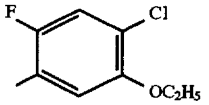 | $CH_3$ | CN | O | S | 60 |
| 8 | IA | 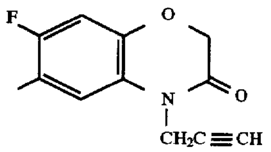 | $CH_3$ | $C_2H_5$ | O | S | 117 |
| 9 | IA | 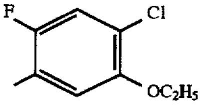 | $CH_3$ | 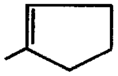 | O | S | 95 |
| 10 | IA | 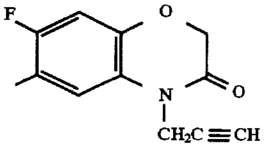 | $CH_3$ | $-CH_2C\equiv CH$ | O | S | 147 |
| 11 | IA | 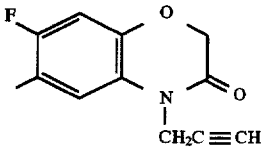 | $CH_3$ | $-CH_2CH=CH_2$ | O | S | 119 |
| 12 | IA | 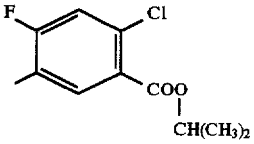 | $CH_3$ | $CH_3$ | O | S | 72 |
| 13 | IA | 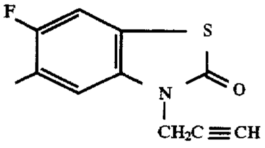 | $CH_3$ | $CH_3$ | O | S | 121 |

TABLE 1-continued
Examples of the compounds of the formula (I)
| Ex. No. | Gen. formula | Ar | R | $R^2$ | Q | A | Melting point (C.) |
|---|---|---|---|---|---|---|---|
| 14 | IA | 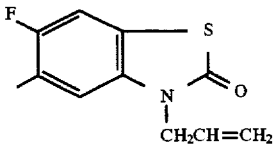 | $CH_3$ | $CH_3$ | O | S | 54 |
| 15 | IA | 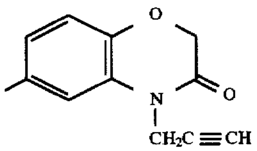 | $CH_3$ | $CH_3$ | O | S | 156 |
| 16 | IA | 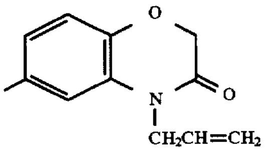 | $CH_3$ | $CH_3$ | O | S | (oil) |
| 17 | IA | 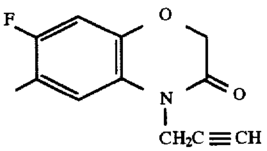 | $CH_3$ | $CHF_2$ | O | S | |
| 18 | IA | 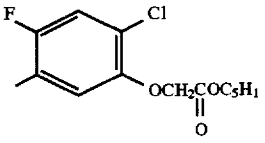 | $CH_3$ | $CH_3$ | O | S | (amorphous) |
| 19 | IA | 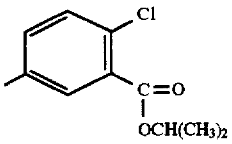 | $CH_3$ | $CH_3$ | O | S | 68 |
| 20 | IA | 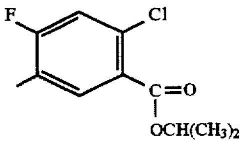 | $CH_3$ | $CHF_2$ | O | S | |
| 21 | IB | 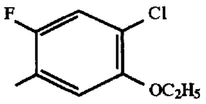 | $CH_3$ | $CH_3$ | O | S | 64 |
| 22 | IB | 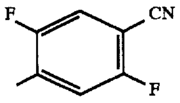 | $CH_3$ | $CH_3$ | O | S | 105 |
| 23 | IA | 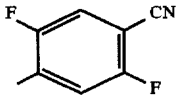 | $CH_3$ | H | O | S | 248 |
| 24 | IA | 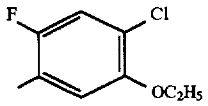 | $CH_3$ | H | O | S | 137 |

TABLE 1-continued
Examples of the compounds of the formula (I)
| Ex. No. | Gen. formula | Ar | R | $R^2$ | Q | A | Melting point (C.) |
|---|---|---|---|---|---|---|---|
| 25 | IA | 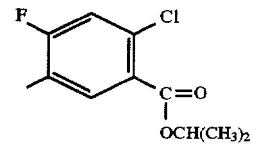 | $CH_3$ | H | O | S | 67 |
| 26 | IA | 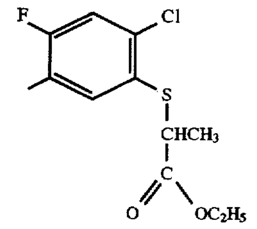 | $CH_3$ | H | O | S | (oil) |
| 27 | IA | 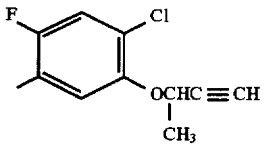 | $CH_3$ | H | O | S | 194 |
| 28 | IA | 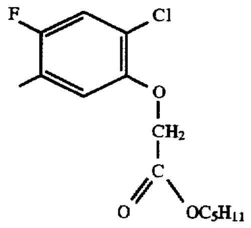 | $CH_3$ | H | O | S | (oil) |
| 29 | IA | 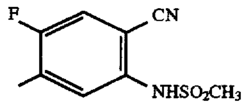 | $CH_3$ | H | O | S | 72 |
| 30 | IA | 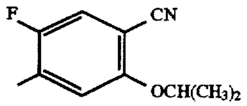 | $CH_3$ | H | O | S | 161 |
| 31 | IA | 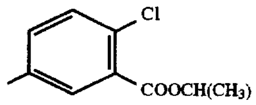 | $CH_3$ | H | O | S | 115 |
| 32 | IA | 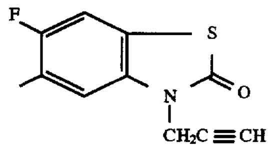 | $CH_3$ | H | O | S | 70 |
| 33 | IA | 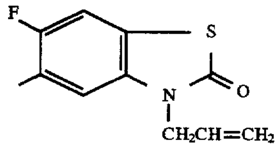 | $CH_3$ | H | O | S | 134 |

TABLE 1-continued
Examples of the compounds of the formula (I)
| Ex. No. | Gen. formula | Ar | R | $R^2$ | Q | A | Melting point (C.) |
|---|---|---|---|---|---|---|---|
| 34 | IA | 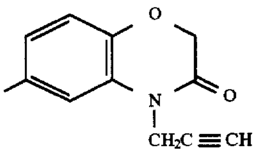 | $CH_3$ | H | O | S | 158 |
| 35 | IA | 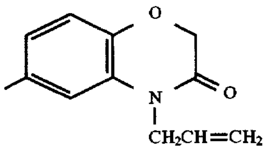 | $CH_3$ | H | O | S | 144 |
| 36 | IB | 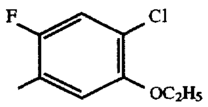 | $CH_3$ | $C_2H_5$ | O | S | 97 |
| 37 | IB | 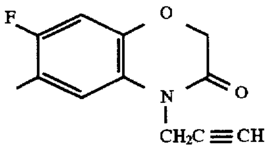 | $CH_3$ | $CHF_2$ | O | S | 119 |
| 38 | IA | 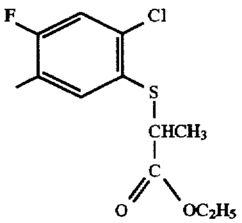 | $CH_3$ | $CH_3$ | O | S | (amorphous) |
| 39 | IA | 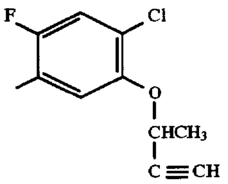 | $CH_3$ | $CH_3$ | O | S | 125 |
| 40 | IA | 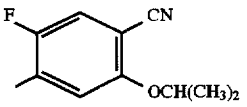 | $CH_3$ | $CH_3$ | O | S | 72 |
| 41 | IB | 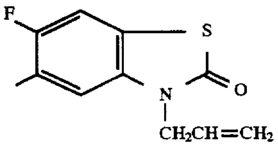 | $CH_3$ | $CHF_2$ | O | S | (amorphous) |
| 42 | IA | 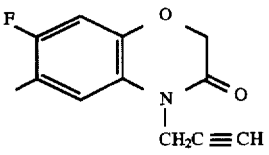 | $C_2H_5$ | $C_2H_5$ | O | S | 137 |

TABLE 1-continued
Examples of the compounds of the formula (I)
| Ex. No. | Gen. formula | Ar | R | $R^2$ | Q | A | Melting point (C.) |
|---|---|---|---|---|---|---|---|
| 43 | IA | 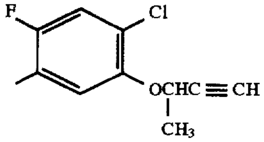 | $CH_3$ | $CHF_2$ | O | S | |
| 44 | IB | 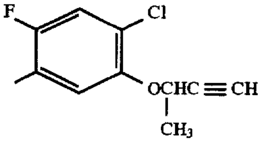 | $CH_3$ | $CHF_2$ | O | S | |
| 45 | IA | 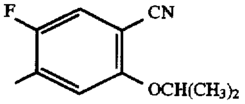 | $CH_3$ | $CH_3$ | S | S | 117 |
| 46 | IA | 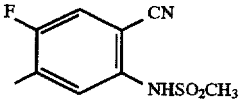 | $CH_3$ | $CH_3$ | S | S | 233 |
| 47 | IA | 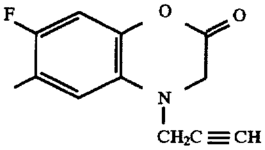 | $CH_3$ | $CH_3$ | S | S | 128 |
| 48 | IA | 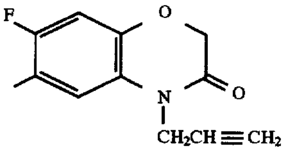 | $CH_3$ | $CH_3$ | S | S | 102 |
| 49 | IA | 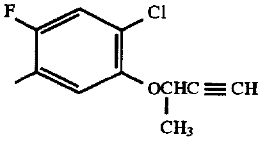 | $CH_3$ | $CH_3$ | S | S | 90 |
| 50 | IA | 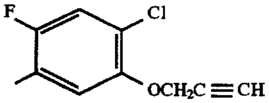 | $CH_3$ | $CH_3$ | S | S | 128 |
| 51 | IA | 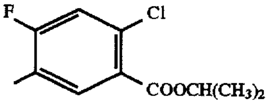 | $C_2H_5$ | $C_2H_5$ | S | S | |
| 52 | IA | 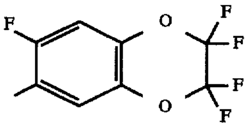 | $CH_3$ | $CH_3$ | S | S | 61 |
| 53 | IA | 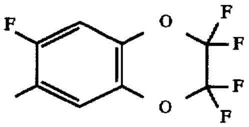 | $C_2H_5$ | $C_2H_5$ | S | S | 67 |

TABLE 1-continued
Examples of the compounds of the formula (I)
| Ex. No. | Gen. formula | Ar | R | $R^2$ | Q | A | Melting point (C.) |
|---|---|---|---|---|---|---|---|
| 54 | IA | 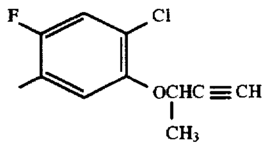 | $C_2H_5$ | $C_2H_5$ | S | S | |
| 55 | IA | 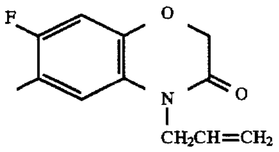 | $C_2H_5$ | $C_2H_5$ | S | S | 155 |
| 56 | IA | 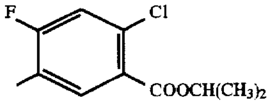 | $CH_3$ | $CH_3$ | S | S | 84 |
| 57 | IB | 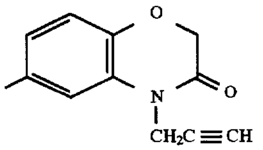 | $CH_3$ | $CHF_2$ | O | S | |
| 58 | IA | 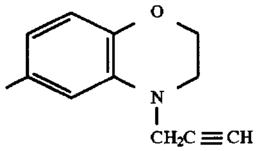 | $CH_3$ | $CHF_2$ | O | S | |
| 59 | IB | 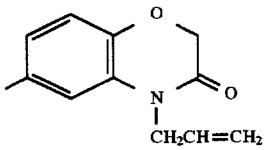 | $CH_3$ | $CHF_2$ | O | S | |
| 60 | IA | 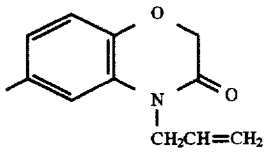 | $CH_3$ | $CHF_2$ | O | S | |
| 61 | IA | 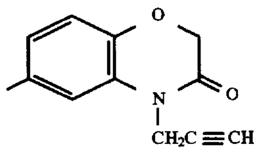 | $CH_3$ | $-CH_2C\equiv CH$ | O | S | 114 |
| 62 | IA | 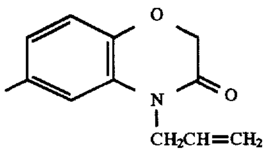 | $CH_3$ | $-CH_2C\equiv CH$ | O | S | 106 |
| 63 | IA | 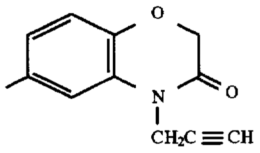 | $CH_3$ | $-CH_2CH\equiv CH_2$ | O | S | (amorphous) |

TABLE 1-continued

Examples of the compounds of the formula (I)

| Ex. No. | Gen. formula | Ar | R | $R^2$ | Q | A | Melting point (C.) |
|---|---|---|---|---|---|---|---|
| 64 | IA | 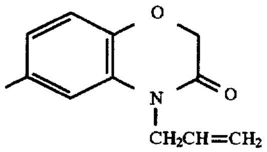 | $CH_3$ | $-CH_2CH \equiv CH_2$ | O | S | (amorphous) |
| 65 | IB | 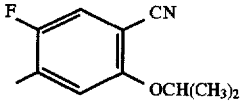 | $CH_3$ | $CHF_2$ | O | S | (amorphous) |
| 66 | IB | 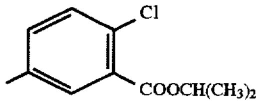 | $CH_3$ | $CHF_2$ | O | S | (amorphous) |
| 67 | IA | 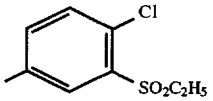 | $CH_3$ | $CH_3$ | O | S | (amorphous) |
| 68 | IA | 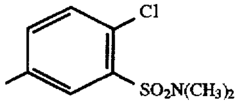 | $CH_3$ | $CH_3$ | O | S | (amorphous) |
| 69 | IB | 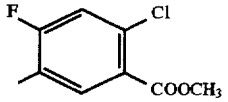 | $CH_3$ | $CHF_2$ | O | S | |
| 70 | IB | 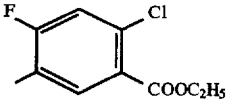 | $CH_3$ | $CHF_2$ | O | S | |
| 71 | IA | 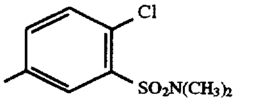 | $CH_3$ | H | O | S | |
| 72 | IA | 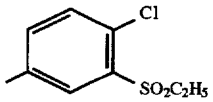 | $CH_3$ | H | O | S | |
| 73 | IA | 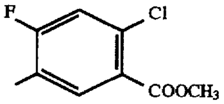 | $CH_3$ | H | O | S | |

Starting Materials of the Formula (II):

EXAMPLE (II-1)

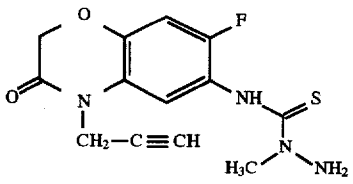

Step 1

A stirred mixture of 12 g (0.12 mol) of calcium carbonate, 150 ml of water, 13.7 g (0.12 mol) of thiophosgene and 100 ml of dichloromethane is treated with 26.4 g (0.12 mol) of 6-amino-7-fluoro-3,4-dihydro-3-ox propargyl-(2H)-1,4-benzoxazine in 50 ml of dichloromethane. The reaction mixture is stirred for approximately 3 hours at 35 C. to 40 C. Then, after filtration, the organic phase is separated off, dried using magnesium sulphate and filtered. The filtrate is freed from solvent in vacuo.

This gives 27 g (85.9% of theory) of 6-isothiocyanato-7-fluoro-3,4-dihydro-3-oxo-4-propargyl-(2H)-1,4-benzoxazine. Melting point: 128 C.

Step 2

A solution of 5.24 g (20 mMol) of 6-isothiocyanato-7-fluoro-3,4-dihydro-3-oxo-4-propargyl-(2H) 1,4-benzoxazine in 60 ml of tetrahydrofuran is treated at 5 C. to 10 C. with 0.92 g (20 mMol) of methylhydrazine. After the mixture has been stirred for two hours at 10 C., the solvent is stripped off in vacuo and the solid residue is recrystallized from iso-propanol.

This gives 4.7 g (76.3% of theory) of 2-methyl-4-(7-fluoro-3,4-dihydro-3-oxo-4-propargyl-(2H)-1,4-benzoxazin-6-yl)-thiosemicarbazide. Melting point: 162 C.

Other examples of compounds of the formula (II)—and/or tautomers thereof—which can be prepared analogously to Example (II-1) are those given in Table 2 below.

TABLE 2

Examples of the compounds of the formula (II)

| Ex. No. | Ar | R | $R^2$ | A | Melting point (C.) |
|---|---|---|---|---|---|
| II-2 | 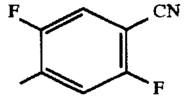 | $CH_3$ | H | S | 173 |
| II-3 | 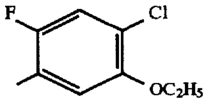 | $CH_3$ | H | S | 154 |
| II-4 | 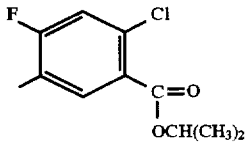 | $CH_3$ | H | S | 125 |
| II-5 | 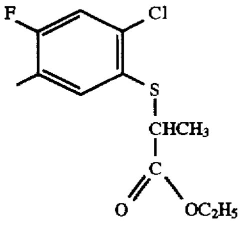 | $CH_3$ | H | S | (oil) |
| II-6 | 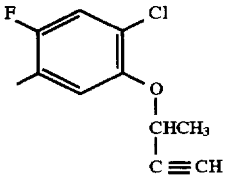 | $CH_3$ | H | S | 154 |
| II-7 | 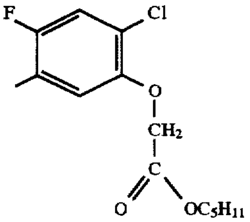 | $CH_3$ | H | S | 111 |
| II-8 | 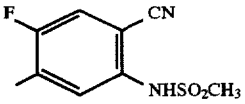 | $CH_3$ | H | S | 187 |

TABLE 2-continued

Examples of the compounds of the formula (II)

| Ex. No. | Ar | R | $R^2$ | A | Melting point (C.) |
|---|---|---|---|---|---|
| II-9 | 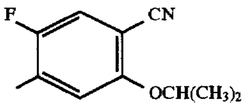 | $CH_3$ | H | S | 166 |
| II-10 | 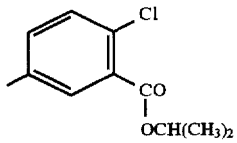 | $CH_3$ | H | S | 116 |
| II-11 | 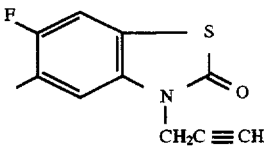 | $CH_3$ | H | S | 157 |
| II-12 | 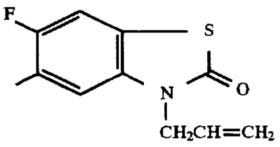 | $CH_3$ | H | S | 161 |
| II-13 | 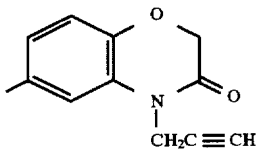 | $CH_3$ | H | S | 152 |
| II-14 | 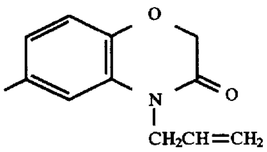 | $CH_3$ | H | S | 118 |
| II-15 | 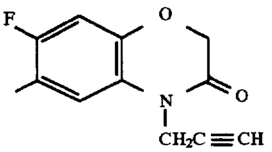 | H | H | S | 164 |
| II-16 | 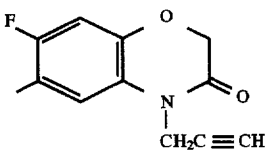 | $C_2H_5$ | $C_2H_5$ | S | |
| II-17 | 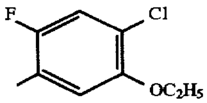 | H | H | S | 129 |
| II-18 | 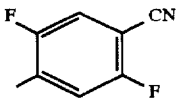 | H | H | S | 240 |

TABLE 2-continued

Examples of the compounds of the formula (II)

| Ex. No. | Ar | R | $R^2$ | A | Melting point (C.) |
|---|---|---|---|---|---|
| II-19 | 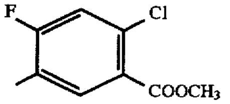 | H | H | S | |

Use Examples

EXAMPLE A

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. After three weeks, the degree of damage to the plants is rated in % damage in comparison to the development of the untreated control.

The figures denote:

0%=no action (like untreated control)

100%=total destruction

EXAMPLE B

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control.

The figures denote:

0%=no action (like untreated control)

100%=total destruction

TABLE A

Post-emergence test/greenhouse

| Active compound | Rate of application g/ha | Wheat | Abutilon | Amaranthus | Datura | Ipomoea | Solanum | Viola |
|---|---|---|---|---|---|---|---|---|
| 5 | 30 | 10 | 100 | 100 | 100 | 100 | 100 | 100 |
| 6 | 30 | 5 | 95 | 100 | 100 | 100 | 100 | 100 |
| 2 | 30 | 20 | 100 | 100 | 100 | 100 | 100 | 100 |
| 8 | 30 | 20 | 100 | 100 | 100 | 100 | 100 | 100 |

TABLE B

Pre-emergence test/greenhouse

| Active compound | Rate of application g/ha | Barley | Abutilon | Chenopodium | Galinsoga | Matricaria | Portulaca | Solanum |
|---|---|---|---|---|---|---|---|---|
| 5 | 125 | 10 | 100 | 95 | 90 | 100 | 100 | 100 |
| 6 | 60 | 20 | 95 | 100 | 80 | 70 | 95 | 95 |
| 2 | 125 | 10 | 100 | 100 | 100 | 100 | 100 | 100 |
| 8 | 125 | 10 | 100 | 100 | 100 | 100 | 100 | 100 |
| 3 | 125 | 0 | 100 | 100 | 100 | 95 | 100 | 100 |

We claim:

1. Substituted aryliminoheterocycles of the general formula (I)

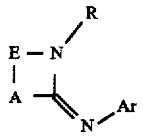

(I)

in which

A represents oxygen or sulphur

E represents one of the following groups

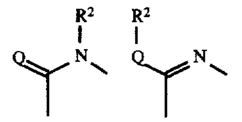

where

Q represents oxygen or sulphur and $R^2$ represents hydrogen, cyano, or represents alkyl having 1 to 6 carbon atoms which is optionally substituted by cyano, halogen, $C_1$–$C_4$-alkoxy, $C_1$–$C_4$-alkyl-carbonyl or $C_1$–$C_4$-alkoxy-carbonyl, or represents alkenyl or alkinyl each of which has 2 to 6 carbon atoms and each of which is optionally substituted by halogen, or represents cycloalkyl having 3 to 6 carbon atoms or cycloalkenyl having 5 or 6 carbon atoms, each of which is optionally substituted by halogen or $C_1$–$C_4$-alkyl, R represents alkyl having 1 to 6 carbon atoms which is optionally substituted by cyano, halogen, $C_1$–$C_4$-alkoxy, $C_1$–$C_4$-alkyl-carbonyl or $C_1$–$C_4$-alkoxy-carbonyl, or represents alkenyl or alkinyl each of which has 2 to 6 carbon atoms and each of which is optionally substituted by halogen, and Ar represents one of the monocyclic or bicyclic aryl or heteroaryl groups below,

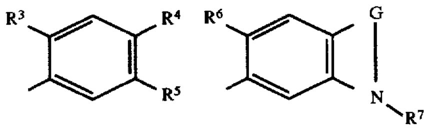

each of which is optionally substituted, and in which $R^3$ represents hydrogen or halogen, $R^4$ represents cyano, nitro, thiocarbamoyl, halogen, or in each case optionally halogen-substituted $C_1$–$C_4$-alkyl or $C_1$–$C_4$-alkoxy, $R^5$ represents the group below $—A^1—A^2—A^3$ in which $A^1$ represents a single bond, or represents oxygen, sulphur, —SO—, —$SO_2$—, —CO— or the group —N—$A^4$— where $A^4$ represents hydrogen, hydroxyl, $C_1$–$C_4$-alkyl, $C_1$–$C_4$-alkoxy, phenyl, $C_1$–$C_4$-alkylsulphonyl or phenylsulphonyl or $A^1$ furthermore represents $C_1$–$C_6$-alkanediyl, $C_2$–$C_6$-alkenediyl, $C_2$–$C_6$-azaalkenediyl, $C_2$–$C_6$-alklinediyl, $C_3$–$C_6$-cycloalkanediyl, $C_3$–$C_6$-cycloalkenediyl or phenylene, each of which is optionally substituted by fluorine, chlorine or bromine, $A^2$ represents a single bond, or represents oxygen, sulphur, —SO—, —$SO_2$—, —CO— or the group —N—$A^4$— where $A^4$ represents hydrogen, hydroxyl, $C_1$–$C_4$-alkyl, $C_1$–$C_4$-alkoxy, phenyl, $C_1$–$C_4$-alkylsulphonyl or phenylsulphonyl or $A^2$ furthermore represents $C_1$–$C_6$-alkanediyl, $C_2$–$C_6$-alkenediyl, $C_2$–$C_6$-azaalkenediyl, $C_2$–$C_6$-alkinediyl, $C_3$–$C_6$-cycloalkanediyl, $C_3$–$C_6$-cycloalkenediyl or phenylene, each of which is optionally substituted by fluorine, chlorine or bromine, $A^3$ represents hydrogen, hydroxyl, amino, cyano, isocyano, thiocyanato, nitro, carboxyl, carbamoyl, thiocarbamoyl, sulpho, chlorosulphonyl, halogen, or represents alkyl, alkoxy, alkylthio, alkylsulphonyl, alkylsulphonyl, alkylamino, dialkylamino, alkoxycarbonyl or dialkoxy(thio)phosphoryl, each of which has 1 to 6 carbon atoms in the alkyl groups and each of which is optionally substituted by halogen or $C_1$–$C_4$-alkoxy, or represents alkenyl, alkenyloxy, alkenylamino, alkylidenamino, alkenyloxycarbonyl, alkinyl, alkinyloxy, alkinylamino or alkinyloxycarbonyl, each of which has 2 to 6 carbon atoms in the alkenyl, alkylidene or alkinyl groups and each of which is optionally substituted by halogen or represents cycloalkyl, cycloalkyloxy, cycloalkylalkyl, cycloalkylalkoxy, cycloalkylidenamino, cycloalkyloxycarbonyl or cycloalkylalkoxy-carbonyl, each of which has 3 to 6 carbon atoms in the cycloalkyl groups and, if appropriate, 1 to 4 carbon atoms in the alkyl groups and each of which is optionally substituted by halogen, cyano, carboxyl, $C_1$–$C_4$-alkyl and/or $C_1$–$C_4$-alkoxycarbonyl, or represents phenyl, phenyloxy, phenyl-$C_1$–$C_4$-alkyl, phenyl-$C_1$–$C_4$-alkoxy, phenyloxycarbonyl or phenyl-$C_1$–$C_4$-alkoxycarbonyl, each of which is optionally substituted by nitro, cyano, carboxyl, halogen $C_1$–$C_4$-alkyl, $C_1$–$C_4$-halogenoalkyl, $C_1$–$C_4$-alkoxy, $C_1$–$C_4$-halogenoalkyloxy and/or $C_1$–$C_4$-alkoxy-carbonyl, (in each case optionally fully or partially hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolyl-$C_1$–$C_4$-alkyl, furyl-$C_1$–$C_4$-alkyl, thienyl-$C_1$–$C_4$-alkyl, oxazolyl-$C_1$–$C_4$-alkyl, isoxazol-$C_1$–$C_4$-alkyl, thiazol-$C_1$–$C_4$-alkyl, pyridinyl-$C_1$–$C_4$-alkyl, pyrimidinyl-$C_1$–$C_4$-alkyl, pyrazolylmethoxy, furylmethoxy, or represents perhydropyranylmethoxy or pyridylmethoxy, $R^6$ represents hydrogen or halogen, $R^7$ represents hydrogen, hydroxyl, or represents alkyl having 1 to 6 carbon atoms which is optionally substituted by cyano, halogen, $C_1$–$C_4$-alkoxy, $C_1$–$C_4$-alkyl-carbonyl or $C_1$–$C_4$-alkoxy-carbonyl, or represents alkenyl or alkinyl, each of which has 2 to 6 carbon atoms and each of which is optionally substituted by halogen, or represents cycloalkyl or cycloalkylalkyl, each of which has 3 to 6 carbon atoms in the cycloalkyl moiety and, if appropriate, 1 to 4 carbon atoms in the alkyl moiety and each of which is optionally substituted by halogen or $C_1$–$C_4$-alkyl, or represents alkoxy or alkenyloxy, each of which has up to 6 carbon atoms and each of which is optionally substituted by halogen, or represents benzyl or benzyloxy, each of which is optionally substituted by cyano, halogen, $C_1$–$C_4$-alkyl, $C_1$–$C_4$-halogenoalkyl, $C_1$–$C_4$-alkoxy or $C_1$–$C_4$-halogenoalkoxy, and G represents one of the following groups —O—CO—, —S—CO—, —O—$C(R^8,R^9)$—CO—, —$C(R^8,R^9)$—O—CO—, —$C(R^8,R^9)$—$C(R^8,R^9)$—, —$C(R^8,R^9)$—$C(R^8,R^9)$—CO—, —$C(R^8)$=$C(R^8)$—, —$C(R^8)$=$C(R^8)$—CO—, —$C(R^8,R^9)$—CO—, —$N(R^{10})$—$C(R^8,R^9)$—CO—, —$C(R^8)$=N—, —O—CO—$C(R^8,R^9)$— where $R^8$ and $R^9$ are identical or different and individually represent hydrogen or alkyl having 1 to 6 carbon atoms or together represent alkanediyl having 2 to 6 carbon atoms, and $R^{10}$ represents hydrogen or alkyl having 1 to 6 carbon atoms.

2. Substituted aryliminoheterocycles of the general formula (I) according to claim 1, in which A represents oxygen or sulphur, E represents one of the following groups

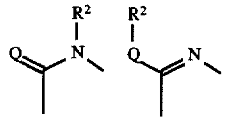

where

Q represents oxygen or sulphur and $R^2$ represents hydrogen, cyano, or represents methyl, ethyl, n- or i-propyl, n-, i-, s- or t-butyl, each of which is optionally substituted by cyano, fluorine, chlorine, methoxy, ethoxy, acetyl, propionyl, methoxycarbonyl or ethoxycarbonyl, or represents propenyl, butenyl, propinyl or butinyl, each of which is optionally substituted by fluorine, chlorine or bromine, or represents cyclopentenyl or cyclohexenyl, R represents methyl, ethyl, n- or i-propyl, n-, i-, s- or t-butyl, each of which is optionally substituted by cyano, fluorine, chlorine, methoxy, ethoxy, acetyl, propionyl, methoxycarbonyl or ethoxycarbonyl, or represents propenyl, butenyl, propinyl or butinyl, each of which is optionally substituted by fluorine, chlorine or bromine, and Ar represents one of the monocyclic or bicyclic aryl or heteroaryl groups below,

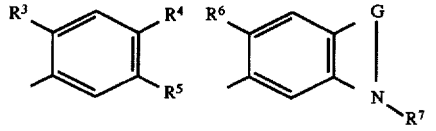

each of which is optionally substituted, in which $R^3$ represents hydrogen, fluorine or chlorine, $R^4$ represents cyano, chlorine, bromine, methyl or trifluoromethyl, $R^5$ represents the group below $$—A^1—A^2—A^3$$

in which $A^1$ represents a single bond, or represents oxygen, sulphur, —SO—, —$SO_2$—, —CO— or the group —N—$A^4$— where $A^4$ represents hydrogen, hydroxyl, methyl, ethyl, n- or i-propyl, methoxy, ethoxy, n- or i-propoxy, methylsulphonyl or ethylsulphonyl, or $A^1$ furthermore represents methylene, ethane-1,1-diyl, ethane-1,2-diyl, propane-1,1-diyl, propane-1-2-diyl, propane-1-3-diyl, ethene-1,2diyl, propene-1,2-diyl, propene-1-3-diyl, ethine-1,2-diyl or propine-1-3-diyl, $A^2$ represents a single bond, or represents oxygen, sulphur, —SO—, —$SO_2$—, —CO— or the group —N—$A^4$— where $A^4$ represents hydrogen, hydroxyl, methyl, ethyl, n- or i-propyl, methoxy, ethoxy, n- or i-propoxy, methylsulphonyl, ethylsulphonyl, n- or i-propylsulphonyl or phenylsulphonyl, or $A^2$ furthermore represents methylene, ethane-1,1-diyl, ethane-1,2diyl, propane-1,1-diyl, propane-1-2-diyl, propane-1-3-diyl, ethene-1,2-diyl, propene-1,2-diyl, propene-1-3-diyl, ethine-1,2-diyl, propine-1,2-diyl or propine-1-3-diyl, $A^3$ represents hydrogen, hydroxyl, amino, cyano, nitro, carboxyl, carbamoyl, sulpho, fluorine, chlorine, bromine, or represents methyl, ethyl, n- or i-propyl, n-, i-, s- or t-butyl, n-, i-, s- or t-pentyl, methoxy, ethoxy, n- or i-propoxy, n-, i-, s- or t-butoxy, n-, i-, s- or t-pentyloxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, methoxycarbonyl, ethoxycarbonyl, n- or i-propoxycarbonyl, dimethoxyphosphoryl, diethoxyphosphoryl, dipropoxyphosphoryl or diisopropoxy-phosphoryl, each of which is optionally substituted by fluorine, chlorine, methoxy or ethoxy, or represents propenyl, butenyl, propenyloxy, butenyloxy, propenylamino, butenylamino, propylidenamino, butylidenamino, propenyloxycarbonyl, butenyloxycarbonyl, propinyl, butinyl, propinyloxy, butinyloxy, propinylamino, butinylamino, propinyloxycarbonyl or butinyloxycarbonyl, each of which is optionally substituted by fluorine or chlorine, or represents cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl, cyclohexylmethyl, cyclo-propylmethoxy, cyclobutylmethoxy, cyclopentylmethoxy, cyclohexylmethoxy, cyclopentylidenamino, cyclohexylidenamino, cyclopentyloxy-carbonyl, cyclohexyloxycarbonyl, cyclopentylmethoxycarbonyl or cyclohexylmethoxycarbonyl, each of which is optionally substituted by fluorine, chlorine, cyano, carboxyl, methyl, ethyl, n- or i-propyl, methoxycarbonyl or ethoxycarbonyl, or represents phenyl, phenyloxy, benzyl, phenylethyl, benzyloxy, phenyloxycarbonyl, benzyloxycarbonyl, (in each case optionally fully or partially hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolylmethyl, furylmethyl, thienylmethyl, oxazolylmethyl, isoxazolmethyl, thiazolmethyl, pyridinylmethyl, pyrimidinylmethyl, pyrazolylmethoxy, furylmethoxy or pyridylmethoxy, each of which is optionally substituted by nitro, cyano, carboxyl, fluorine, chlorine, bromine, methyl, ethyl, n- or i-propyl, trifluoromethyl, methoxy, ethoxy, n- or i-propoxy, difluoromethoxy, trifluoromethoxy, methoxycarbonyl and/or ethoxycarbonyl, $R^6$ represents hydrogen, fluorine or chlorine, $R^7$ represents hydrogen, hydroxyl, or represents methyl, ethyl, n- or i-propyl, n-, i-, s- or t-butyl, each of which is optionally substituted by cyano, fluorine, chlorine, methoxy, ethoxy, acetyl, propionyl, methoxycarbonyl or ethoxycarbonyl, or represents propenyl, butenyl, propinyl or butinyl, each of which is optionally substituted by fluorine, chlorine or bromine, or represents cyclopropyl, cyclobutyl, cyclopentyl, cyclohexyl, cyclopropylmethyl cyclobutylmethyl, cyclopentylmethyl or cyclohexylmethyl, each of which is optionally substituted by fluorine, chlorine, bromine, methyl or ethyl, or represents methoxy, ethoxy, n- or i-propoxy, n-, i- or s-butoxy, propenyloxy or butenyloxy, each of which is optionally substituted by fluorine and/or chlorine, or represents benzyl or benzyloxy, each of which is optionally substituted by cyano, fluorine, chlorine, bromine, methyl, ethyl, trifluoromethyl, methoxy, ethoxy, difluoromethoxy or trifluoromethoxy, and G represents one of the following groups —O—CO—, —S—CO—, —O—C($R^8$,$R^9$)—CO—, —C($R^8$,$R^9$)—O—CO—, —C($R^8$,$R^9$)—C($R^8$,$R^9$)—, —C($R^8$)=C($R^8$)—, —C($R^8$,$R^9$)—CO—, —N($R^{10}$)—C($R^8$,$R^9$)—CO—, —C($R^8$)=N—, —O—CO—C($R^8$,$R^9$)— where $R^8$ and $R^9$ are identical or different and individually represent hydrogen, methyl, ethyl, n- or i-propyl or together represent ethane-1,2-diyl, and $R^{10}$ represents hydrogen, methyl, ethyl, n- or i-propyl.

3. Process for the preparation of substituted arylimino-heterocycles of the general formula (I)

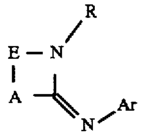

(I)

in which A, E, R and Ar have the meanings given in claim 1, characterized in that arylimino compounds of the general formula (II)

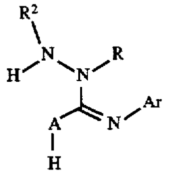

(II)

in which

A, R, $R^2$ and Ar have the abovementioned meanings—and compounds which are tautomeric to these—are cyclized with reactive carbonic acid derivatives of the general formula (III)

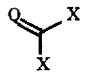

(III)

in which

Q has the abovementioned meaning and

X represents halogen, alkoxy, aryloxy or aralkoxy, if appropriate in the presence of a reaction auxiliary and if appropriate in the presence of a diluent, and, if appropriate, the resulting compounds of the formulae (IA) and (IB), in the event that $R^2$ in these formulae is hydrogen, are reacted with alkylating agents of the general formula (IV)

$$R^2—X^1 \quad (IV)$$

in which $R^2$ has the abovementioned meaning with the exception of hydrogen and $X^1$ represents halogen or the group —O—$SO_2$—O—$R^2$, if appropriate in the presence of a reaction auxiliary and if appropriate in the presence of a diluent.

4. A method of controlling unwanted vegetation which comprises applying to such vegetation or to a locus from which it is desired to exclude such vegetation a herbicidally effective amount of a compound according to claim 1.

5. A herbicidal composition comprising a herbicidally effective amount of a compound according to claim 1 and a surfactant.

* * * * *